(12) United States Patent
Siewerdsen et al.

(10) Patent No.: US 11,790,525 B2
(45) Date of Patent: Oct. 17, 2023

(54) METHOD FOR METAL ARTIFACT AVOIDANCE IN X-RAY IMAGING

(71) Applicants: THE JOHNS HOPKINS UNIVERSITY, Baltimore, MD (US); Siemens Healthcare GmbH, Erlangen (DE)

(72) Inventors: Jeffrey H. Siewerdsen, Baltimore, MD (US); Pengwei Wu, Baltimore, MD (US); Niral M. Sheth, Baltimore, MD (US); Bjoern W. Kreher, Erlangen (DE)

(73) Assignees: THE JOHNS HOPKINS UNIVERSITY, Baltimore, MD (US); SIEMENS HEALTHCARE GMBH, Erlangen (DE)

( * ) Notice: Subject to any disclaimer, the term of this patent is extended or adjusted under 35 U.S.C. 154(b) by 215 days.

(21) Appl. No.: 17/112,812

(22) Filed: Dec. 4, 2020

(65) Prior Publication Data

US 2021/0174502 A1 Jun. 10, 2021

Related U.S. Application Data

(60) Provisional application No. 62/944,615, filed on Dec. 6, 2019.

(51) Int. Cl.
*G06T 7/00* (2017.01)
*A61B 6/12* (2006.01)
(Continued)

(52) U.S. Cl.
CPC .............. *G06T 7/0012* (2013.01); *A61B 6/12* (2013.01); *A61B 6/4441* (2013.01);
(Continued)

(58) Field of Classification Search
CPC .......... G06T 7/0002; G06T 7/74; A61B 6/12; A61B 6/4441
See application file for complete search history.

(56) References Cited

U.S. PATENT DOCUMENTS 6,580,777 B1 *   6/2003  Ueki ................... A61B 6/4447
                                                              378/15
6,721,387 B1     4/2004  Naidu et al.
(Continued)

FOREIGN PATENT DOCUMENTS

DE   102017206946 A1 *  7/2018
EP         1627601 A1 *  2/2006  ............. A61B 6/032
JP       2012040284 A  *  3/2012  ............. A61B 6/508

OTHER PUBLICATIONS

Machine translation of JP-2012040284-A (Year: 2012).*
(Continued)

*Primary Examiner* — John Villecco
*Assistant Examiner* — Courtney Joan Nelson
(74) *Attorney, Agent, or Firm* — MH2 TECHNOLOGY LAW GROUP LLP

(57) ABSTRACT

A system and method for metal artifact avoidance in 3D x-ray imaging is provided. The method includes determining a 3D location of metal in an object or volume of interest to be scanned; estimating a source-detector orbit that will reduce the severity of metal artifacts; moving an imaging system to locations consistent with the source-detector orbit that was estimated; and scanning the object according to the source-detector orbit.

20 Claims, 25 Drawing Sheets

(51) Int. Cl.
A61B 6/00 (2006.01)
G06T 7/70 (2017.01)
G06T 11/00 (2006.01)

(52) U.S. Cl.
CPC .......... *A61B 6/4447* (2013.01); *A61B 6/5205* (2013.01); *A61B 6/5258* (2013.01); *G06T 7/70* (2017.01); *G06T 11/005* (2013.01); *G06T 11/006* (2013.01); *G06T 2207/10081* (2013.01); *G06T 2207/20084* (2013.01); *G06T 2207/30004* (2013.01)

(56) References Cited

U.S. PATENT DOCUMENTS

| | | | |
|---|---|---|---|
| 8,233,586 | B1 | 7/2012 | Boas |
| 8,503,750 | B2 | 8/2013 | Benson et al. |
| 2013/0070991 | A1* | 3/2013 | Yang ................ G06T 11/008 382/131 |
| 2016/0078647 | A1 | 3/2016 | Schildkraut et al. |
| 2016/0163071 | A1 | 6/2016 | Han et al. |
| 2017/0238897 | A1* | 8/2017 | Siewerdsen ............ A61B 6/466 |
| 2018/0137658 | A1 | 5/2018 | Zhang et al. |

OTHER PUBLICATIONS

Gary H. Glover, Norbert J. Pelc, "An algorithm for the reduction of metal clip artifacts in CT reconstructions", General Electric Company, Medical Systems Division, Applied Science Laboratory, Apr. 21, 1981, 10 pages. (Year: 1981).*
Machine translation of DE-102017206946-A1 (Year: 2018).*
N. Hansen and S. Kern, Evaluating the CMA Evolution Strategy on Multimodal Test Functions, in Parallel Problem Solving from Nature—PPSN VIII, edited by X. Yao, E.K. Burke, J.A. Lozano, et al. (Springer Berlin Heidelberg, Berlin, Heidelberg, 2004), pp. 282-291.
S. Zhao, D. D. Robeltson, G. Wang, B. Whiting, and K. T. Bae, "X-ray CT metal artifact reduction using wavelets: an application for imaging total hip prostheses," IEEE transactions on medical imaging, vol. 19, No. 12, pp. 1238-1247, 2000.
M. Bal and L. Spies, "Metal artifact reduction in CT using tissue-class modeling and adaptive prefiltering," Medical physics, vol. 33, No. 8, pp. 2852-2859, 2006.
Yu, Lifeng PhD; Li, Hua PhD; Mueller, Jan MS; Kofler, James M. PhD; Liu, Xin PhD; Primak, Andrew N. PhD; Fletcher, Joel G. MD; Guimaraes, Luis S. MD; Macedo, Thanila MD; McCollough, Cynthia H. PhD Metal Artifact Reduction From Reformatted Projections for Hip Prostheses in Multislice Helical Computed Tomography: Techniques and Initial Clinical Results, Investigative Radiology: Nov. 2009—vol. 44—Issue 11—p. 691-696.
E. Meyer, R. Raupach, M. Lell, B. Schmidt, and M. Kachelries, "Normalized metal artifact reduction (NMAR) in computed tomography," Medical physics, vol. 37, No. 10, pp. 5482-5493, 2010.
E. Meyer, R. Raupach, M. Lell, B. Schmidt, and M. Kachelries, "Frequency split metal artifact reduction (FSMAR) in computed tomography," Medical Physics, vol. 39, No. 4, pp. 1904-1916, Apr. 2012.
Subhas, N., Primak, A.N., Obuchowski, N.A. et al. Iterative metal artifact reduction: Evaluation and optimization of technique. Skeletal Radiol 43, 1729-1735 (2014). https://doi.org/10.1007/s00256-014-1987-2.
R. Pua, S. Wi, M. Park, J.-R. Lee, and S. Cho, "An Image-Based Reduction of Metal Artifacts in Computed Tomography," Journal of Computer Assisted Tomography, vol. 40, No. 1, p. 131, Feb. 2016.
B. D. Man, J. Nuyts, P. Dupont, G. Marchal, and P. Suetens, "Reduction of metal streak artifacts in X-ray computed tomography using a transmission maximum a posteriori algorithm," IEEE Transactions on Nuclear Science, vol. 47, No. 3, pp. 977-981, Jun. 2000.

B. D. Man, J. Nuyts, P. Dupont, G. Marchal, and P. Suetens, "An iterative maximum-likelihood polychromatic algorithm for CT," IEEE transactions on medical imaging, vol. 20, No. 10, pp. 999-1008, 2001.
I. A. Elbakri and J. A. Fessler, "Segmentation-free statistical image reconstruction for polyenergetic X-ray computed tomography," in Proceedings IEEE International Symposium on Biomedical Imaging, 2002, pp. 828-831.
F. Morsbach, S. Bickelhaupt, G. A. Wanner, A. Krauss, B. Schmidt, and H. Alkadhi, "Reduction of metal artifacts from hip prostheses on CT images of the pelvis: value of iterative reconstructions," Radiology, vol. 268, No. 1, pp. 237-244, 2013.
Nasirudin, Radin & Mei, Kai & Penchev, Petar & Fehringer, Andreas & Pfeiffer, Franz & Rummeny, Ernst & Fiebich, Martin & Noël, Peter. (2015). Reduction of Metal Artifact in Single Photon-Counting Computed Tomography by Spectral-Driven Iterative Reconstruction Technique. PLOS One. 10. e0124831. 10.1371/journal.pone.0124831.
Aissa, J., Boos, J., Schleich, C., Sedlmair, M., Krzymyk, K., Kröpil, P., Antoch, G., & Thomas, C. (2017). Metal Artifact Reduction in Computed Tomography After Deep Brain Stimulation Electrode Placement Using Iterative Reconstructions. Investigative radiology, 52(1), 18-22.
J. W. Stayman, Y. Otake, J. L. Prince, A. J. Khanna, and J. H. Siewerdsen, "Model-based tomographic reconstruction of objects containing known components," IEEE transactions on medical imaging, vol. 31, No. 10, pp. 1837-1848, 2012.
V. Ruth, D. Kolditz, C. Steiding, and W. A. Kalender, "Metal Artifact Reduction in X-ray Computed Tomography Using Computer-Aided Design Data of Implants as Prior Information," Investigative radiology, vol. 52, No. 6, pp. 349-359, 2017.
X. Uneri, T. Yi, X. Zhang, J. W. Stayman, P. Helm, G. M. Osgood, N. Theodore, J. H. Siewerdsen "3D-2D Known-Component Registration for Metal Artifact Reduction in Cone-Beam CT," presented at the International Conference on Image Formation in X-Ray Computed Tomography, 2018, p. 4.
Herbst, M., Schebesch, F., Berger, M., Choi, J. H., Fahrig, R., Hornegger, J., & Maier, A. (2015). Dynamic detector offsets for field of view extension in C-arm computed tomography with application to weight-bearing imaging. Medical physics, 42(5), 2718-2729.
Tornai MP, McKinley RL, Brzymialkiewicz CN, Madhav P, Cutler SJ, Crotty DJ, Bowsher JE, Samei E, Floyd CE. Design and Development of a Fully-3D Dedicated X-ray Computed Mammotomography System. Medical Imaging 2005: Physics of Medical Imaging. In: Flynn MichaelJ., editor. Proceedings of SPIE. vol. 5745. Bellingham, WA: SPIE; 2005. pp. 189-197.
Y. Ye and G. Wang, "Filtered backprojection formula for exact image reconstruction from cone-beam data along a general scanning curve," Medical Physics, vol. 32, No. 1, pp. 42-48, 2005.
J. W. Stayman and J. H. Siewerdsen, "Task-based trajectories in iteratively reconstructed interventional cone-beam CT," Proc. 12th Int. Meet. Fully Three-Dimensional Image Reconstr. Radiol. Nucl. Med, pp. 257-260, 2013.
S. Ouadah, M. Jacobson, J. W. Stayman, T. Ehtiati, C. Weiss, and J. H. Siewerdsen, "Task-Driven Orbit Design and Implementation on a Robotic C-Arm System for Cone-Beam CT," Proc SPIE Int Soc Opt Eng, vol. 10132, Mar. 2017.
P. M. Joseph and R. D. Spital, "A method for correcting bone induced artifacts in computed tomography scanners.," Journal of computer assisted tomography, vol. 2, No. 1, pp. 100-108, 1978.
J. H. Siewerdsen, D. J. Moseley, S. Burch, S. K. Bisland, A. Bogaards, B. C. Wilson, D. A. Jaffray, "Volume CT with a flat-panel detector on a mobile, isocentric C-arm: Pre-clinical investigation in guidance of minimally invasive surgery," Medical physics, vol. 32, No. 1, pp. 241-254, 2005.
W. Zbijewski, P. De Jean, P. Prakash, Y. Ding, J. W. Stayman, N. Packard, R. Senn, D. Yang, J. Yorkston, A. MacHado, J. A. Carrino, J. H. Siewerdsen "A dedicated cone-beam CT system for musculoskeletal extremities imaging: Design, optimization, and initial performance characterization," Medical physics, vol. 38, No. 8, pp. 4700-4713, 2011.

(56) References Cited

OTHER PUBLICATIONS

R. Baba, K. Ueda, and M. Okabe, "Using a flat-panel detector in high resolution cone beam CT for dental imaging," Dentomaxillofacial radiology, vol. 33, No. 5, pp. 285-290, 2004.

L. A. Feldkamp, L. C. Davis, and J. W. Kress, "Practical cone-beam algorithm," Josa a, vol. 1, No. 6, pp. 612-619, 1984.

Gary H. Glover, Norbert J. Pelc, "An algorithm for the reduction of metal clip artifacts in CT reconstructions", General Electric Company, Medical Systems Division, Applied Science Laboratory, Apr. 21, 1981, 10 pages.

\* cited by examiner

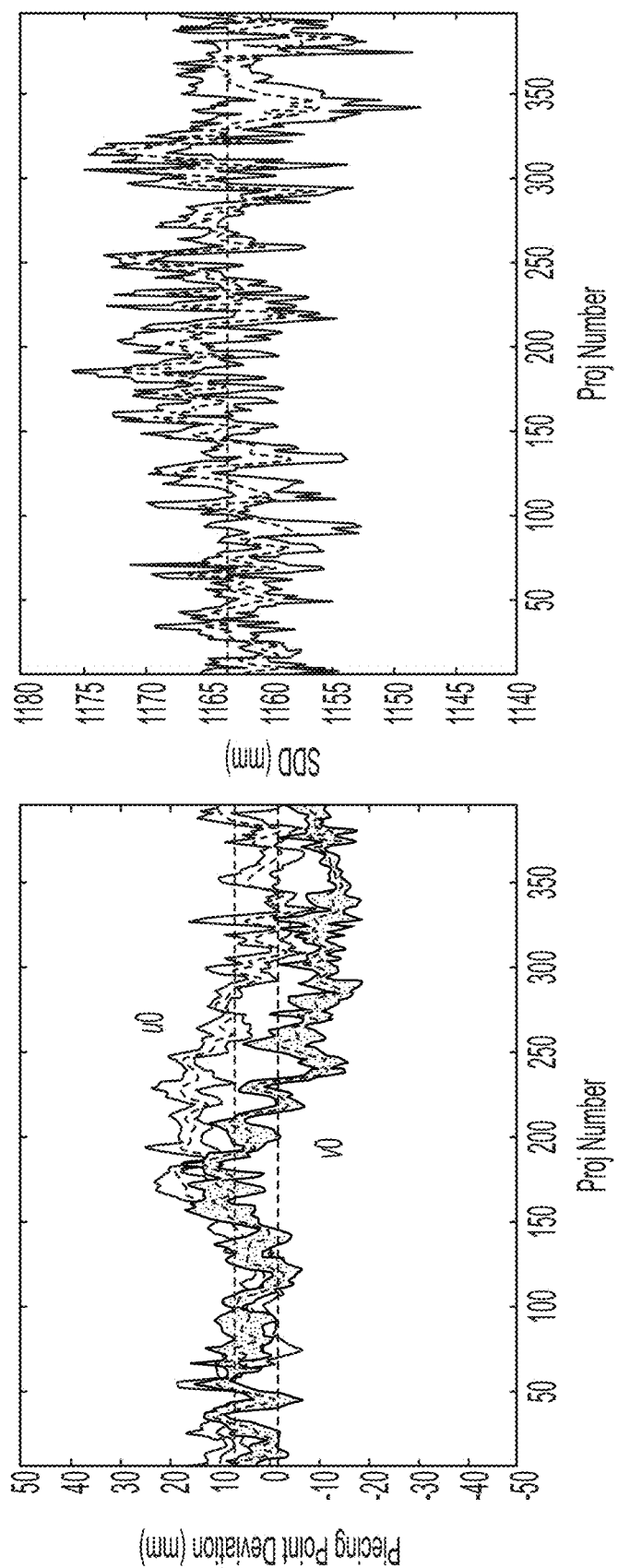

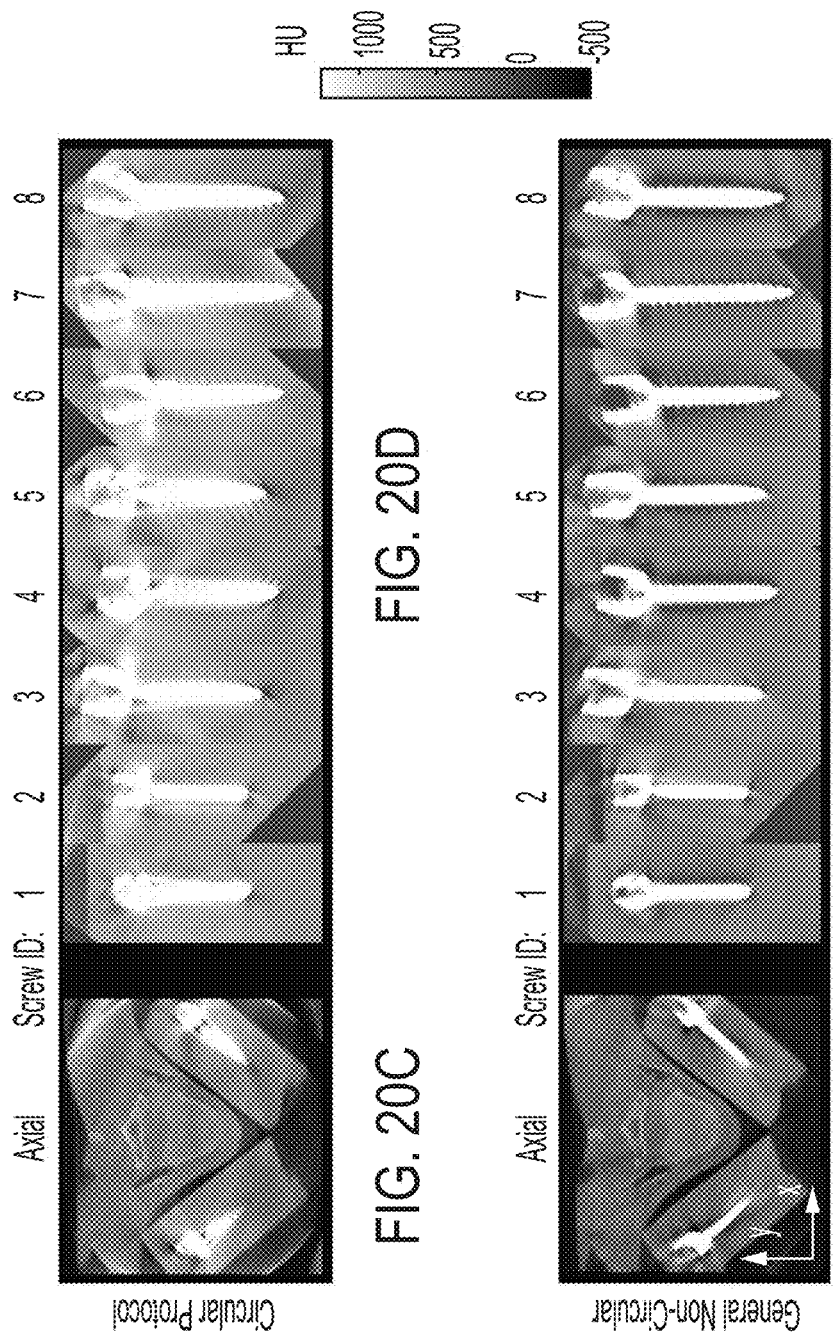

METHOD FOR METAL ARTIFACT AVOIDANCE IN X-RAY IMAGING

CROSS-REFERENCE TO RELATED APPLICATIONS

This application claims priority to U.S. Provisional Application No. 62/944,615 filed on Dec. 6, 2019, the disclosure of which is hereby incorporated by reference in its entirety.

FIELD

The present teachings generally relate x-ray imaging and more particularly to a system and a method for metal artifact avoidance in x-ray imaging.

BACKGROUND

3-D volumetric x-ray imaging e.g., x-ray computed tomography (CT) or cone-beam CT (CBCT)—is a prevalent means of imaging the body in diagnostic and image-guided medical procedures. CT is a mainstay of diagnostic radiology, and CBCT systems have emerged for a variety of specialized applications, including diagnostic imaging in dental, ENT, orthopedic, and breast imaging and for interventional guidance in image-guided surgery, interventional radiology, and image-guided radiation therapy. Such CBCT systems offer benefits of portability, small footprint, low cost, and capability for both fluoroscopy and 3D imaging. The primary area of application for the invention described below is CBCT image-guided surgery, where metal implants in the body often pose a limitation to image quality. Secondary applications include other areas of CBCT imaging (e.g., specialty diagnostic imaging systems in dental, ENT, or orthopedic imaging) and potentially some applications of CT (e.g., interventional CT and/or diagnostic CT).

Among the factors that challenge image quality in CT and CBCT are image artifacts arising from high-density objects (e.g., metal), such as surgical clips and staples, dental fillings, surgical instruments, orthopedic implants, etc. Such objects cause various image artifacts (generally referred to as "metal artifacts") that can obscure useful information about the imaged tissue and hinder delineation of the metal objects themselves. An example scenario in intraoperative imaging is the need to precisely visualize the placement of a metal instrument (e.g., an implanted screw) in relation to surrounding anatomy for guidance, navigation, and validation of surgical device placement. A large number and/or high-density of metal objects in the field-of-view (FOV) can severely degrade image quality and confound visualization of nearby anatomy and confirmation of device placement.

The aforementioned artifacts include dark and bright bands and streaks typically referred to as metal artifacts. Such artifacts are attributable to several effects, including beam-hardening (shift in the x-ray energy spectrum that introduces errors or biases in detector signal), x-ray scatter (a high-proportion of scattered x-rays contributing to detector signal in the highly attenuating region of metal objects), and photon starvation (a small number of x-ray photons contributing to detector signal in the highly attenuating region of metal objects). Moreover, such effects are sensitive to geometric instability and geometric calibration error of the imaging system (particularly for mobile CBCT systems, which are mechanically less stable compared to fixed-gantry CT or CBCT systems).

Recognizing the important challenge associated with metal artifacts, numerous approaches have been proposed and implemented for metal artifact reduction (MAR), each with varying advantages and some shortcomings. MAR algorithms are generally software-based and can be considered in the following broad categories: (1) those that modify the measured projection data within metal-affected regions by a correction of detector pixel values (e.g., interpolation/inpainting). Such methods are generally referred to as projection-domain metal artifacts correction (PMAC); 2) those that invoke a model of the physics of the sources of the artifacts (e.g., x-ray spectral beam hardening) and improve image quality using iterative model-based image reconstruction (MBIR); and (3) those that use prior information of the metal objects (e.g. exact shape of the object) or the patient (e.g. prior CT/MRI scans) in combination with (1) and/or (2).

Drawbacks of such MAR methods include: (1) errors in metal-affected region localization and/or detector pixel value correction; (2) errors in modeling of the x-ray beam or other physics of the source of the artifacts; (3) the requirement for prior information about the metal objects or the patient, which may be unavailable or difficult to obtain; and (4) a potentially large computational burden if iterative algorithm is involved. Despite decades of research and development on MAR methods and their deployment in a variety of commercially available clinical CT and CBCT systems, metal artifacts persist as a major source of image degradation.

There is a need to develop techniques that overcomes the above-noted deficiencies. Moreover, such methods perform better when the quality of x-ray projection data acquired in the 3D scan is higher—i.e., when the x-ray projection data are less affected by noise, error, and/or bias associated with metal objects in the volume of interest. That is to say, MAR methods perform better when there is less artifact to correct. This invention provides a methodology to accomplish this, providing x-ray projection data that are less affected by metal objects (i.e., carry reduced noise, error, and/or bias) such that resulting 3D image reconstructions will exhibit reduced metal artifact, which can possibly obviate the need for MAR, and/or that application of MAR methods may work better than with projection data acquired in a conventional manner.

SUMMARY

In accordance with examples of the present disclosure, a method for metal artifact avoidance in 3D x-ray imaging is provided. The method comprises determining a 3D location of metal in an object or volume of interest to be scanned; estimating a source-detector orbit that will reduce the severity of metal artifacts; moving an imaging system to locations consistent with the source-detector orbit that was estimated; and scanning the object according to the source-detector orbit. In some examples, since the system typically does not know the existing spatial constraints (like table position, patient size, tools, etc) the estimated location might not be feasible. So, the system can support the user in moving the imaging system to an optimal location regarding the estimated location as well as the spatial constraint.

Various additional features can be implemented in the computer-implemented method including the following. The determining can further comprise one or more of the following: performing an initial 3D scan of the object or volume of interest, acquiring one or more x-ray projection images of the object or volume of interest, using one or more previously acquired x-ray images, or using a tracking system comprising one or more cameras or electromagnetic trackers to locate the metal. The source-detector orbit can comprise a position and orientation of an x-ray source and a detector for projections to be acquired in the in 3D x-ray imaging. The estimating the source-detector orbit further comprises computing an objective function that is based on the 3D location of the metal that was determined, wherein the objective function describes a characteristic that is associated with metal artifacts in 3D image reconstruction. The characteristic can comprise an estimation of a spectral shift, an attenuation, or combinations thereof. The objective function can based on one or more of: a standard deviation of a metric map along a rotation axis of a gantry, a maximum of the metric map along the rotation axis of the gantry, a sum of metric maps for a range of rotation angles of the gantry. The severity of metal artifacts can be reduced compared to a circular path in a plane perpendicular to a long axis of the object. The scanning can further comprise acquiring a plurality of x-ray projections along the source-detector orbit and forming a 3D image reconstruction of the object. The forming the 3D image reconstruction can further comprise performing one or more 3D image reconstruction algorithms comprising 3D filtered backprojection or model-based image reconstruction.

In accordance with examples of the present disclosure, a 3-D x-ray imaging system is provided. The 3D x-ray imaging system can comprise a 3-D x-ray imaging device comprising a gantry that is movable in a plurality of tilt angles along a tilt axis and a plurality of rotation angles along a rotation axis; and a hardware-processor configured to execute instructions comprising: determining a 3D location of metal in an object or volume of interest to be scanned; estimating a source-detector orbit that will reduce the severity of metal artifacts; moving an imaging system to locations consistent with the source-detector orbit that was estimated; and scanning the object according to the source-detector orbit.

Various additional features can be implemented in the computer-implemented method including the following. The determining can further comprise one or more of the following: performing an initial 3D scan of the object or volume of interest, acquiring one or more x-ray projection images of the object or volume of interest, using one or more previously acquired x-ray images or using a tracking system comprising one or more cameras or electromagnetic trackers to locate the metal. The source-detector orbit can comprise a position and orientation of an x-ray source and a detector for projections to be acquired in the in 3D x-ray imaging. The estimating the source-detector orbit further can comprise computing an objective function that is based on the 3D location of the metal that was determined, wherein the objective function describes a characteristic that is associated with metal artifacts in 3D image reconstruction. The characteristic can comprise an estimation of a spectral shift, an attenuation, or combinations thereof. The objective function can be based on one or more of: a standard deviation of a metric map along a rotation axis of a gantry, a maximum of the metric map along the rotation axis of the gantry, a sum of metric maps for a range of rotation angles of the gantry. The severity of metal artifacts can be reduced compared to a circular path in a plane perpendicular to a long axis of the object. The scanning can further comprise acquiring a plurality of x-ray projections along the source-detector orbit and forming a 3D image reconstruction of the object. The forming the 3D image reconstruction can further comprise performing one or more 3D image reconstruction algorithms comprising 3D filtered backprojection or model-based image reconstruction.

In accordance with examples of the present disclosure, a non-transitory computer readable medium is provided that comprises instructions that when executed by a hardware processor are configured to perform a method for metal artifact avoidance in 3D x-ray imaging, the method comprising: determining a 3D location of metal in an object or volume of interest to be scanned; estimating a source-detector orbit that will reduce the severity of metal artifacts; moving an imaging system to locations consistent with the source-detector orbit that was estimated; and scanning the object according to the source-detector orbit.

In accordance with examples of the present disclosure, a computer-implemented method for metal artifact avoidance in computed tomography (CT) imaging is provided. The computer-implemented method comprises acquiring a plurality of initial views of a target location of imaged volume to provide an initial guidance in the CT imaging using a CT imaging device; forming, by a hardware processor, a coarse 3D attenuation map of the target location; segmenting, using a segmentation algorithm executed by the hardware processor, the coarse 3D attenuation map into a plurality of images with similar properties; computing, by the hardware processor, a graphical representation that relates to a severity of a metal artifact in the target location; computing, by the hardware processor, an objective function that is defined with respect to a tilt angle of a gantry of the CT imaging device to capture the severity of the metal artifact across a range of rotation angles of the gantry; and determining, by the hardware processor, a desired tilt angle based on the objective function for the gantry at which to perform a 3D image scan of the target location to avoid the metal artifact.

Various additional features can be implemented in the computer-implemented method including the following. The plurality of initial views can comprise a plurality of scout views, wherein a scout view of the plurality of scout views is a mode of operation of the CT imaging device to prescribe CT slices to initial positioning of the CT imaging device. The coarse 3D attenuation map can be formed by backprojecting each of the plurality of scout views. The desired tilt angle can be determined based on determining a minimum of the objective function. The graphical representation can comprise a metric map that relates rotation angles to tilt angles of the gantry. The objective function can be based on a standard deviation of the metric map along a rotation axis of the gantry. The objective function can be based on a maximum of the metric map along a rotation axis of the gantry. The objective function can be based on a sum of metric maps for the range of rotation angles of the gantry. The computer-implemented method can further comprise performing the 3D image scan of the target location based on the desired tilt angle that is determined. The computer-implemented method can further comprise providing the desired tilt angle to an operator of the CT imaging device for which the 3D image scan is performed.

In accordance with examples of the present disclosure, a computed tomography (CT) imaging system is provided that can comprise a CT imaging device comprising a gantry that is movable in a plurality of tilt angles along a tilt axis and a plurality of rotation angles along a rotation axis; and a hardware-processor configured to execute instructions comprising: acquiring a plurality of initial views of a target location of imaged volume to provide an initial guidance in CT imaging using the CT imaging device; forming a coarse 3D attenuation map of the target location; segmenting, using a segmentation algorithm, the coarse 3D attenuation map into a plurality of images with similar properties; computing a graphical representation that relates to a severity of a metal artifact in the target location; computing an objective function that is defined with respect to the tilt angle to capture the severity of the metal artifact across a range of rotation angles of the gantry; and determining a desired tilt angle based on the objective function for the gantry at which to perform a 3D image scan of the target location to avoid the metal artifact.

Various additional features can be implemented in the CT imaging system including the following. The plurality of initial views can comprise a plurality of scout views, wherein a scout view of the plurality of scout views is a mode of operation of the CT imaging device to prescribe CT slices to initial positioning of the CT imaging device. The coarse 3D attenuation map can be formed by backprojecting each of the plurality of scout views. The desired tilt angle is determined based on determining a minimum of the objective function. The graphical representation comprises a metric map that relates rotation angles to tilt angles of the gantry. The objective function is based on a standard deviation of the metric map along a rotation axis of the gantry. The objective function can be based on a maximum of the metric map along a rotation axis of the gantry. The objective function can be based on a sum of metric maps for the range of rotation angles of the gantry. The hardware processor can be further configured to execute instructions comprising performing the 3D image scan of the target location based on the desired tilt angle that is determined. The hardware processor can further configured to execute instructions comprising providing the desired tilt angle to an operator of the CT imaging device for which the 3D image scan is performed.

BRIEF DESCRIPTION OF THE DRAWINGS

The accompanying drawings, which are incorporated in, and constitute a part of this specification, illustrate implementations of the present teachings and, together with the description, serve to explain the principles of the disclosure. In the figures:

FIG. 3A shows volume rendering of a cylindrical water phantom containing various metal spheres and rods. Two scout projection views (AP and Lateral)) of the phantom, corresponding to p(u, v|$\theta$=0, $\phi$=0) and p(u, v|$\theta$=90, $\phi$=0) in the MAA method. FIG. 3B shows backprojected volume (coarse 3D attenuation map, denoted $\mu_c$) from two scout views. FIG. 3C shows simple intensity-based segmentation (called the segmented coarse 3D attenuation map, and denoted $\mu_{seg}$) of high-density metal objects from the attenuation map in FIG. 3B. The dashed-line inset region in FIG. 3C shows a zoomed-in view of one of the segmented regions.

FIG. 7A show the metric map q($\theta$,$\phi$). Note similarity to FIG. 4 (which computed the metric map assuming complete 3D attenuation map of the metal objects). The metric map computed from just 2 views still manages to localize views corresponding to high attenuation (high spectral shift) that will result in metal artifacts. FIG. 7B shows the objective function Q($\phi$) computed from horizontal lines in the metric map of FIG. 7A. This again reproduces the idealized results of FIG. 5, showing desirable tilt angles at ~$\phi$=8° and ~$\phi$=27° (arrows 702 and 704).

FIG. 8A shows two projection scout views, p(u, v|$\theta$=0, $\phi$=0) and p(u, v|$\theta$=90, $\phi$=0). FIG. 8B shows a coarse 3D attenuation map ($\mu_c$) formed by unweighted backprojection of the two scout views in FIG. 8A. FIG. 8C shows intensity-based segmentation of the coarse 3D attenuation map ($\mu_{seg}$). FIG. 8D shows the metric map q($\theta$,$\phi$) computed using Eq. (1) by forward projection of FIG. 8C ($\mu_{seg}$). FIG. 8E shows the objective function Q($\phi$) computed from horizontal lines in FIG. 8D, the minimum in which suggests tilt angles ($\phi^*$) that will avoid metal artifacts.

FIG. 15A and FIG. 15B show the degree of reproducibility in system geometry for the pre-determined non-circular orbit according to examples of the present disclosure.

FIG. 16A shows MTF for the three scenarios defined by the arranged in FIG. 13A and FIG. 13B and FIG. 16B, FIG. 16C, and FIG. 16D show axial and sagittal zoomed-in views (skull-base) of a head phantom for the three scenarios, respectively.

FIG. 19A-FIG. 19C show example axial slice segmentation overlaid with ground truth). Segmentations are shown for varying number of scout views. FIG. 19D shows isosurface of $\mu_{seg}$ computed from two views for the end-to-end method. FIG. 19E shows isosurface of ground truth segmentation (downsampled the same as $\mu_{seg}$).

FIG. 20A-FIG. 20F shows a MAA method applied to a chest phantom implanted with eight pedicle screws according to examples of the present disclosure. FIG. 20A shows the $q(\theta,\phi)$ metric map overlaid with the optimal non-circular orbit. FIG. 20B shows the magnitude of blooming artifact (FWHM of the screw shaft) for each of the 8 screws. Axial images in (FIG. 20C and FIG. 20E) for circular and (MAA) non-circular scans show the improvement in visual image quality acquisition, illustrated further in (FIG. 20D and FIG. 20F) by zoomed quasi-axial slices in-plane with each screw.

Figure 1A:
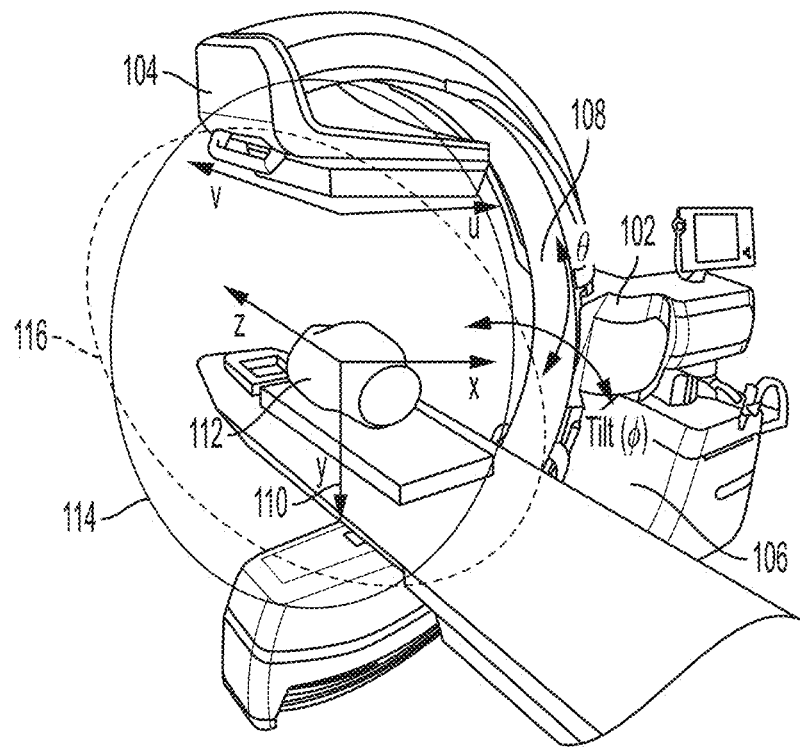
FIG. 1A and FIG. 1B show an illustration of an example system and geometry for MA. The tilt angle ($\phi^*$) defines a circular orbit scan plane that reduces metal artifacts in the 3D image reconstruction.

It should be noted that some details of the figures have been simplified and are drawn to facilitate understanding of the present teachings rather than to maintain strict structural accuracy, detail, and scale.

DETAILED DESCRIPTION

Generally speaking, examples of the present disclosure provide for a system and method for metal artifact avoidance (MAA), which is different than and an improvement over PMAC and MBIR, makes no assumptions of prior information of the patient of metal implants, can be used in combination with PMAC and/or MBIR if desired, and in itself adds little or no computational burden. Specifically, the present system and method provides for MAA by adapting the CT or CBCT image acquisition in a manner that reduces the influence of metal objects on the projection data, and in turn, the severity of metal artifacts. The present system and method may not necessarily give "minimum" or "zero" metal artifact, but provides for less artifact than a conventional scan.

Aspects of the present disclosure are different from previous PMAC approaches in the following ways: (1) The present system and method is a hardware-based solution that instead of correcting metal artifacts in the post-acquisition stage, seeks to avoid metal artifacts in the first place during image acquisition. It is more robust than software-based method and can be easily integrated into current CBCT systems without major modification to the artifacts correction and reconstruction pipeline—i.e., the MAA approach is consistent with (can be used in combination with) existing PMAC methods and (2) Information needed for the automatic trajectory design is obtained through a small plurality (e.g., two) scout views. Unlike some methods mentioned above, no prior information of the metal objects or the patient is needed for the proposed solution, although such prior information can be included—for example, to improve the segmentation step in 208 of FIG. 2. The method for determining the gantry tilt angle based on as few as two scout views. The tilt angle for MAA using a CBCT imaging system is calculated based on as few as two scout views using the methods described below. The tilt angle determination is formed as a simple optimization problem (with respect to $\phi$) with the goal of reducing metal artifacts. The problem is formed in the projection domain for simplicity and computational efficiency.

Usually, CT or CBCT systems acquire projection image data via a circular orbit—i.e., the x-ray source and detector travel in a circle about the patient—and the plane containing that circular orbit is orthogonal to the long axis of the patient. Note the three following points regarding the source-detector orbit:

(i) Previous work has reported various imaging methods involving noncircular orbits—e.g., to expand the FOV to reduce "cone-beam artifacts" (which are wholly distinct from metal artifacts), or to maximize spatial-frequency sampling with respect to a particular imaging task. Noncircular orbits usually involve more sophisticated analytical or iterative (MBIR) methods compared to simple 3D filtered backprojection (which is suitable to circular orbits and is the most common mainstay of CT or CBCT image reconstruction methods).

(ii) Moreover, it is not uncommon for CT or CBCT data to be acquired using a circular orbit that is tilted with respect to the long axis of the patient. In diagnostic CT of the head, for example, the CT scanner gantry is sometimes tilted along the canthomeatal line to reduce beam-hardening effects associated with the petrous bones of the skull. Such a gantry tilt technique is fairly specific to imaging of the skull and is intended to overcome high attenuation in common anatomical sites (and is not geared toward avoidance of metal artifacts). A tilted (circular) orbit is still consistent with 3D filtered backprojection (denoted FBP) and other analytical reconstruction techniques. A non-circular orbit may not be consistent with basic 3D FBP or other analytical reconstruction algorithms. Both circular and non-circular orbits may be generally consistent with typical 3D model-based iterative reconstruction (MBIR) with a knowledge of system geometry. Both circular and non-circular orbits can be reconstructed using a deep learning (DL) neural network, a convolutional neural network (CNN), or other related methods. The MAA method is applicable to all such reconstruction and post-processing methods, since it applies to the data acquisition process, not the reconstruction process per se.

(iii) The MAA method adapts the source-detector orbit in a manner that specifically minimizes the influence of metal objects on the projection data—e.g., signal biases associated with attenuation of the x-ray beam by metal objects. One non-limiting example described below involves a tilted circular (or semicircular) orbit [as in (ii)] and selects the tilt angle in a manner specifically to minimize the effects of highly attenuating metal objects on the projection data (and thereby helps to avoid metal artifacts in the 3D image reconstruction).

In one non-limiting example, MAA involves a titled circular orbit, with the angle of the tilt determined by a small plurality of projection views (e.g., 2 views), referred to as "scout" views. From as few as 2 scout views, a tilted circular orbit can be determined that minimizes the influence of metal on the projection data—i.e., avoids metal artifacts to begin with, rather than correcting them with PMAC or reducing their influence in image reconstruction using MBIR. That said, scans acquired with the MAA method are still compatible with PMAC and/or MBIR and may similarly benefit from the features of both.

Figure 1B:
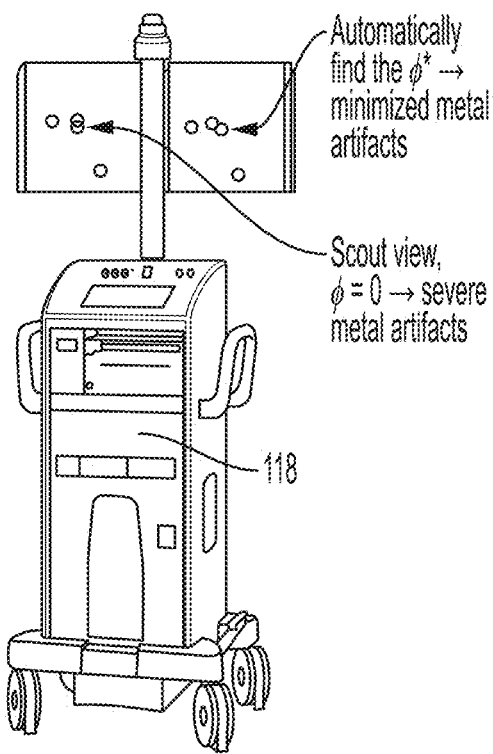

FIG. 1A and FIG. 1B show an illustration of an example system and geometry for MAA in accordance with examples of the present disclosure. FIG. 1A shows CT system 102 with gantry 104, in the form of a mobile C-arm or O-arm, that is movable in at least two degrees of freedom, denoted by tilt angle ($\phi^*$) 106 and rotation angle (v) 108. Tilt angle ($\phi^*$) 106 defines a circular orbit scan plane that reduces metal artifacts in the 3D image reconstruction. The tilt angle can vary from −30° to +30°. The rotation angle can vary from 0° to 196°. Because the C-arm provides motorized control of both tilt angle and rotation angle, non-circular orbits can be executed via computer-controlled variation of the tilt angle and the rotation angle during the scan. For example, a mobile C-arm or O-arm are typical examples of CBCT imaging systems capable of a tilted circular trajectory. For example, a mobile C-arm or O-arm are typical examples of CBCT imaging system that can have an x-ray tube, computer-controlled tube output, and an x-ray detector (for example, a flat-panel detector, FPD) with detector area sufficient to cover a volume of interest in the 3D scan. The system geometry is commonly defined by a source-detector distance (SDD) and source-axis distance (SAD), resulting in a volumetric field-of-view (FOV) covering a volume of interest. A nominal scan protocol involves a plurality of projections acquired over a scan arc of 180° or more at particular settings of x-ray tube output and scan time. Systems suitable to be used in the present disclosure include isocentric or non-isocentric C-arms, O-arms, fixed-room C-arms (e.g., Axiom Artis Zee), or ring gantry diagnostic CT scanners capable of gantry tilt (e.g., Somatom Definition).

FIG. 1A also shows coordinate system (x, y, z) 110 for object 112 being scanned and coordinate system (u, v) 114 for a plane of gantry 104. FIG. 1A also shows a normal (non-tilted) circular trajectory (tilt angle $\phi$=0, shown by circle 114, and a tilted circular trajectory shown by circle 116. FIG. 1B shows diagnostic system 114 that can be coupled with CT system 102, according to examples of the present disclosure. Control system 118 can include a computer system that is used to process and display the results of CT system 102 using the method as described further below.

Figure 2:
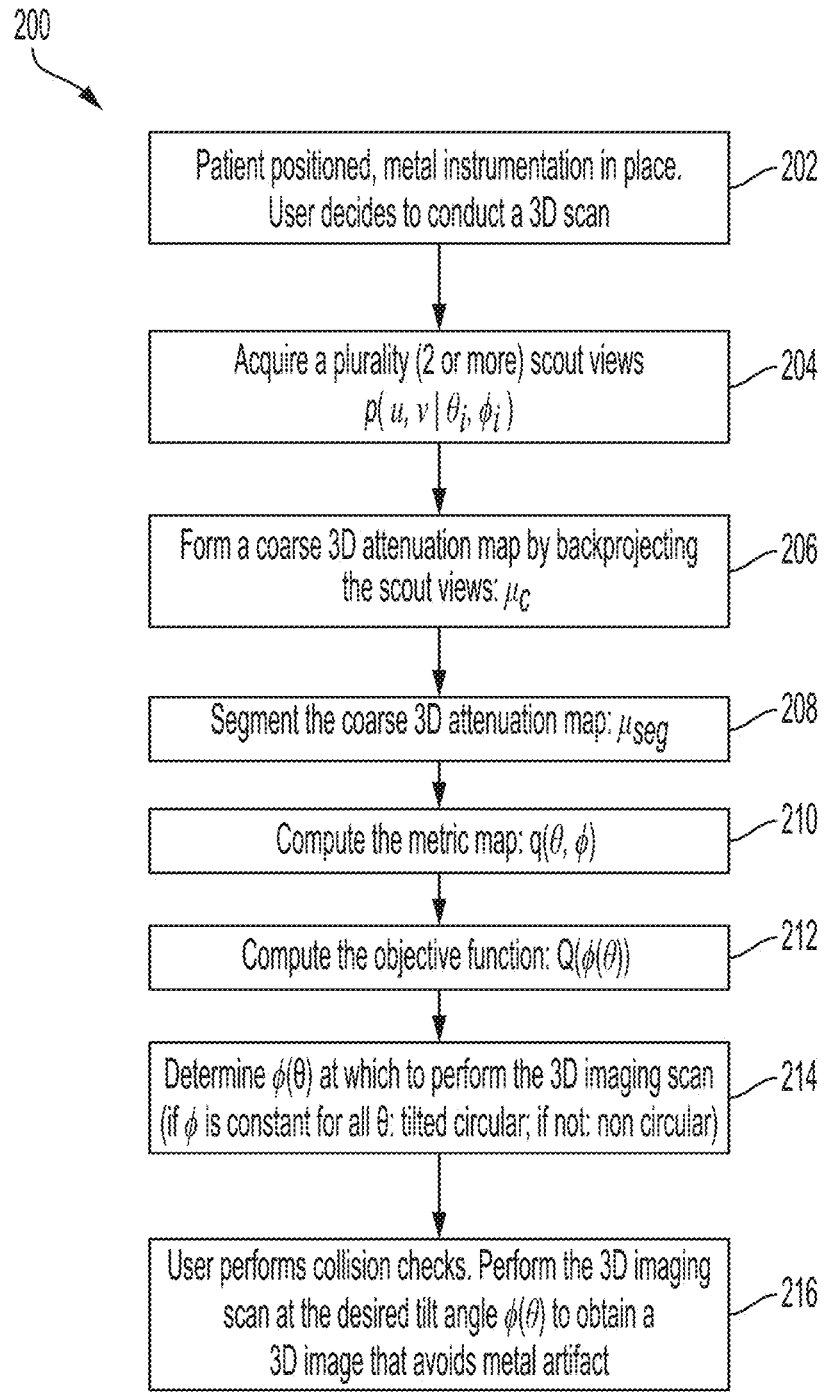
FIG. 2 shows a flowchart of a MAA method according to examples of the present disclosure.

FIG. 2 shows a computer-implemented method 200 for metal artifact avoidance in CT imaging, according to examples of the present disclosure. Prior to beginning method 200, a patient and metal instrumentation are positioned on a table of CT system 102 and a scan is indicated at 202.

Method 200 continues by acquiring, at 204, a plurality (e.g. 2 or more) of scout views along a normal (non-tilted) circular trajectory (tilt angle $\phi$=0, shown by circle 114 in FIG. 1A). Following determination of the tilt angle $\phi^*$, a 3D scan of the patient is performed with this tilted circular trajectory (shown by circle 116 in FIG. 1A). With a nominal non-tilted circular geometry, two scout views (e.g., lateral and AP views, 90 degrees apart) are acquired. Projection views acquired at particular $\theta$ and $\phi$ are denoted as p(u, v|$\theta_i$, $\phi_i$). With this definition, the two scout views (i=1, 2) can be denoted as p(u, v|$\theta$=0, $\phi$=0) and p(u, v|$\theta$=90, $\phi$=0). These scout views can be acquired at very low dose, since they need only depict regions associated with metal objects. Acquisition of standard scout view images at the start of the procedure is typical and imposes no additional workflow or dose to the patient.

Method 200 continues by forming, at 206, a coarse 3D attenuation map ($\mu_c$) by backprojecting the scout view acquired at 204. To localize dense anatomy and metal objects based on acquired scout views, the two scout views are backprojected to form a coarse 3D attenuation map ($\mu_c$), which is then segmented to form a segmented coarse 3D attenuation map ($\mu_{seg}$), containing only the high-attenuation voxels. Segmentation can be performed with simple segmentation methods, such as adaptive thresholding, or more advanced methods based on machine learning, deep learning, convolutional neural networks (CNN), etc.

Method 200 continues by segmenting, at 208, the coarse 3D attenuation map ($\mu_{seg}$) to localize a particularly dense anatomy and/or high-density metal objects. Exemplary methods for determining $\mu_{seg}$ from the coarse attenuation map include (but are not limited to) intensity thresholding, region growing, and artificial neural network based classification. Such segmentation methods can operate with or without prior information regarding the size, shape, number, and/or material content of metal objects known or believed to be within the patient. The tilt angle $\phi$ that minimizes metal artifacts is determined from $\mu_{seg}$. Exemplary methods for determining $\phi$ from $\mu_{seg}$ are detailed below—involving an objective function that is minimized for a particular selection of $\phi$ ($\phi^*$) in the projection domain. Note that the objective function can be minimized through exhaustive search (iterative optimization not required).

In one non-limiting example, the operations described in 204, 206, and 208 are performed in a serial manner, as shown in FIG. 2. This first example is called "single U-Net" in FIG. 18, 19, where the single U-Net operation is marked by 208 in FIG. 2.

Figure 21:
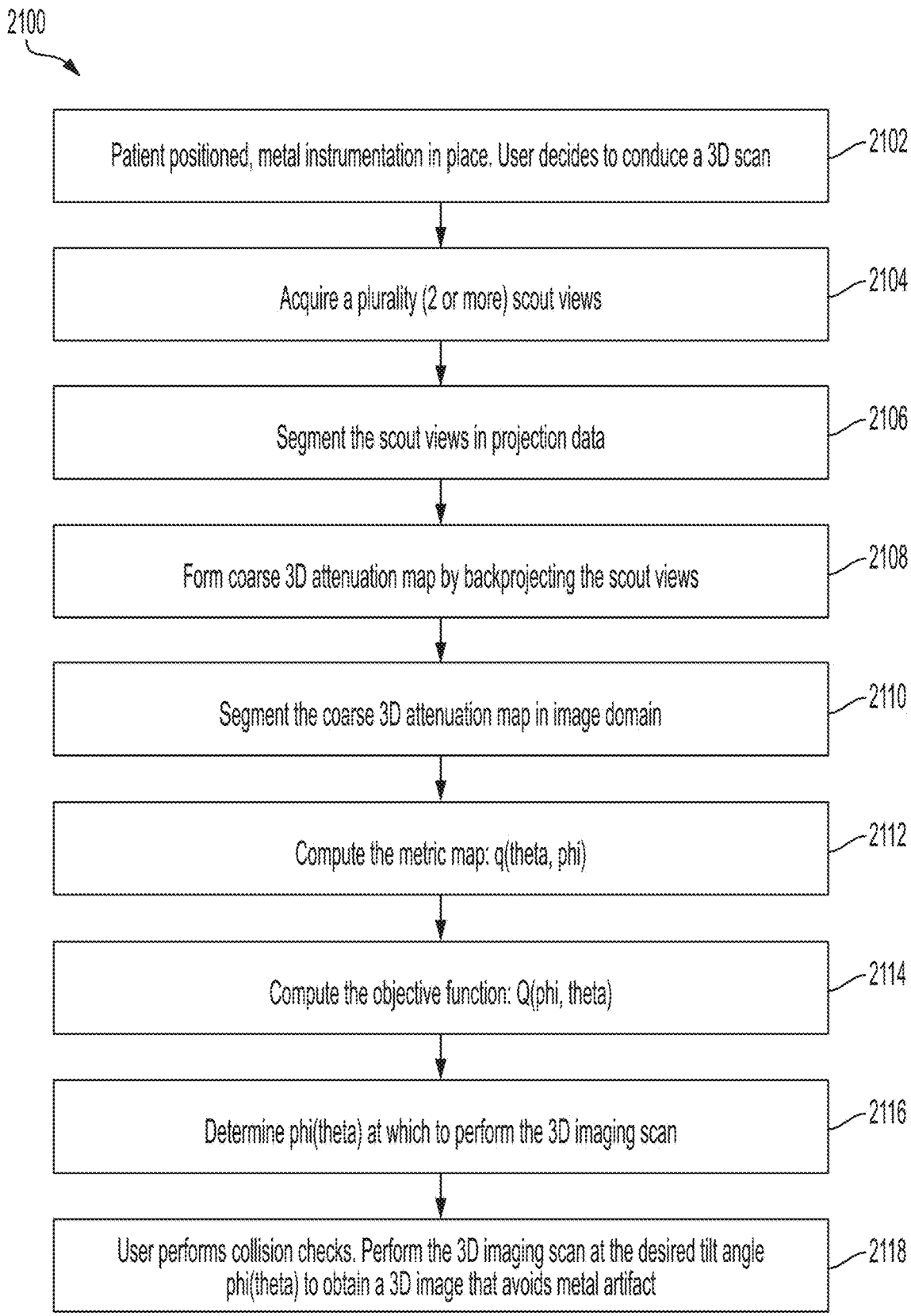
FIG. 21 shows another method show a method for metal artifact avoidance in 3D x-ray imaging according examples of the present disclosure.

In another non-limiting example, the scout views can be segmented to define regions with dense anatomy and high-density metal objects, before being backprojected to form $\mu_c$. This method may potentially improve the accuracy of $\mu_{seg}$, but tends to be challenged by overlapping structures and a very wide dynamic range of signals in projection data. Some methods (e.g., KC-Recon) [15] have been developed to overcome such challenges. This segmentation operation is performed between operations described in 204 and 206 of FIG. 2. This second example is called "Dual U-Net" in FIG. 18, 19. FIG. 21 shows a method 2100 illustrating the Dual U-Net example. As shown in FIG. 21, operations 2102 and 2104 are the same as operations 202 and 204. After the operations of 2104 where a plurality of scout view are acquired, the scout views are segmented in projection domain to contain only particularly dense anatomy and/or high-density metal objects, as in 2106. The method 2100 then continues to form coarse 3D attenuation map by backprojecting the scout view, as in 2108. The method 2100 then continues to segment the coarse 3D attenuation map in the image domain, as in 2110. The operations of 2104 and 2110 represent the "Dual U-Net" nature of this method. The method 2100 then continues to perform operations 2112, 2114, 2116, and 2118 that are the same as described by the operations of 210-216.

In yet another non-limiting example, the coarse 3D attenuation map $\mu_c$ can also be determined via FBP reconstruction of a greater plurality of sparse views (more views compared to the other examples, e.g. 10 views). Instead of doing simple backprojection, FBP implies a "filter" on the projection data prior to backprojection. From studies that have been performed, filtering does not improve the performance for just 2 scout views but does improve performance with a larger number of scout views collected. $\mu_c$ can then be segmented to form $\mu_{seg}$ same as the first example discussed above.

Figure 18:
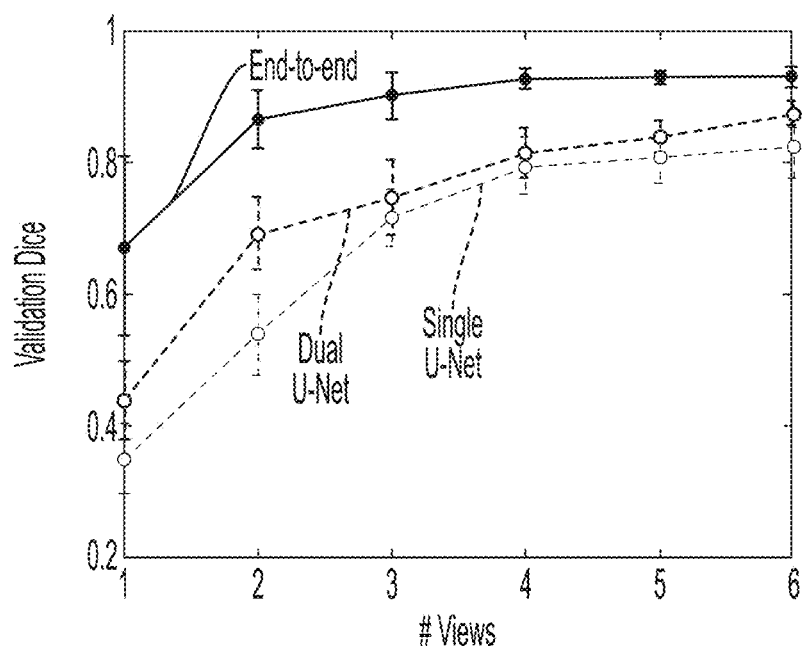
FIG. 18 shows performance of segmenting real or simulated metal implants in terms of Dice Coefficient (denoted DC) in validation testing of three network types (single U-Net, dual U-Net, and End-to-End) as a function of the number of projection views.
Figure 22:
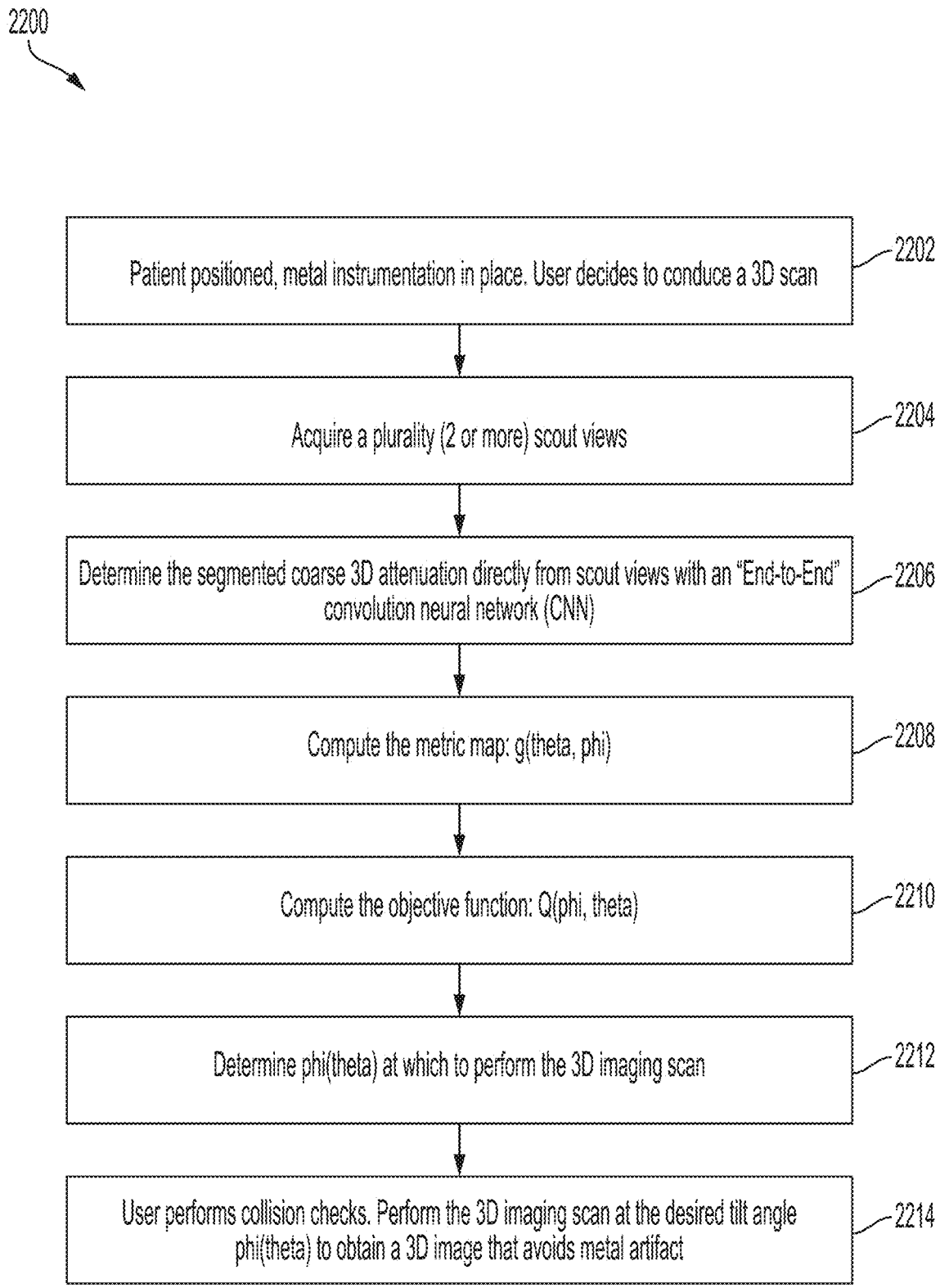
FIG. 22 show a show still another method for metal artifact avoidance in 3D x-ray imaging using a CNN network according examples of the present disclosure.

In yet another non-limiting example, the segmented coarse 3D attenuation seg can be determined directly from scout views with an "End-to-End" convolutional neural network (CNN) approach, as called in FIG. 18,19 and discussed further below, that allows the network to learn the output without explicitly producing an intermediate result—i.e., there is no need to compute $\mu_c$ as an intermediate step. One example design of the "End-to-End" CNN is described in FIG. 14. In this example, the operations described in 206 and 208 are performed in a single operation. FIG. 22 shows a method 2200 illustrating the End-to-End method example. As shown in FIG. 22, operations 2202 and 2204 are the same as operations 202 and 204. After the operations of 2204 where a plurality of scout view are acquired, the "End-to-End" CNN determines the segmented coarse 3D attenuation map, as in 2206 and as described further below. The method 2200 then continues to perform operations 2208, 2010, 2112, and 2114 that are the same as described by the operations of 210-216.

Method 200 continues by computing, at 210, at metric map based on the segmentation of the coarse 3D attenuation map ($\mu_{seg}$). A metric map (denoted as $q(\theta,\phi)$) is defined in the projection domain that relates to the severity of metal artifacts that will result in the 3D image reconstruction. Note that $q(\theta,\phi)$ is defined for each projection view ($\theta$) at each tilt angle ($\phi$), which is all generated by forward projecting $\mu_{seg}$ according to the actual imaging system geometry.

A metric map (denoted as $q(\theta,\phi)$) is defined that relates to the severity of metal artifacts that will result in the 3D image reconstruction. Note that $q(\theta,\phi)$ is defined for each projection view in the projection domain (denoted by 2D spatial coordinates (u,v) of the detector) to avoid time consuming search in the 3D reconstruction domain. Three example definitions of $q(\theta,\phi)$ are described below.

Example 1 (Polyenergetic Shift): Compute the amount of metal (high-density objects) induced beam hardening (BH) artifacts (spectral shift) in projection domain for each rotation angle ($\theta$) and tilt angle ($\phi$):

$$q(\theta, \Phi) = \sum_{u,v} (p_{mono}(u, v | \theta, \Phi) - p_{poly}(u, v | \theta, \Phi)) \quad (1)$$

where $p_{mono}$(u, v|$\theta$, $\phi$) is the simulated monoenergetic line integral value at detector pixel index (u,v), which is determined by forward projecting $\mu_{seg}$ in the previous step, with the forward projection geometry defined by $\theta$ and $\phi$. Since the forward projection operator is monoenergetic, $p_{mono}$(u, v|$\theta$, $\phi$) is without BH artifacts. Therefore, simulated beam hardening artifacts are added using the formula below to generate the corresponding BH contaminated polyenergetic line integral $p_{poly}$(u, v|$\theta$, $\phi$):

$$p_{poly}(u, v | \theta, \Phi) = \sum_{i=1}^{N} \alpha_i p_{mono}^i(u, v | \theta\phi) \quad (2)$$

where $\alpha_i$ are the polynomial coefficients determined by the incident spectrum from the x-ray tube and the attenuation property of the metal object.

Example 2 (Maximum Attenuation): Compute the summation of the k largest monoenergetic line integral for each $\theta$ and $\phi$:

$$q(\theta, \phi) = \sum_k \mathrm{maxk}(p_{mono}(u, v | \theta, \Phi)) \quad (3)$$

where $p_{mono}$(u, v|$\theta$, $\phi$) is the simulated monoenergetic line integral value at detector pixel index (u,v) as above, maxk is an operator that takes k largest value from the argument.

Example 3 (Monoenergetic Threshold): Compute a summation of the monoenergetic line integral values that are above a certain threshold, for each $\theta$ and $\phi$. The thresholding operation can help isolate the effects of high-density metal objects from the low-density anatomy background (soft tissue etc.) in the projection domain.

$$q(\theta, \phi) = \sum_{u,v} Thresh(p_{mono}(u, v | \theta, \phi)) \quad (4)$$

where $p_{mono}$(u, v|$\theta$, $\phi$) is the simulated monoenergetic line integral value at detector pixel index (u,v) as above, Thresh is an operator that takes values from the argument that is above a certain threshold.

Example 4: Compute a summation of the monoenergetic line integral over the entire projection view for each $\theta$ and $\phi$ $$q(\theta, \phi) = \sum_{u,v} p_{mono}(u, v | \theta, \phi) \quad (5)$$

where $p_{mono}$(u, v|$\theta$, $\phi$) is the simulated monoenergetic line integral value at detector pixel index (u,v) as above.

Alternative formulations of the metric map $q(\theta,\phi)$ can certainly be constructed—e.g., a logarithmic transform of any of the examples above.

Example 1 (Equation (1)) is one non-limiting example in the MAA solution described here. Simulation and phantom experiments show this formulation to provide reliable avoidance of metal artifacts (especially the beam hardening component of metal artifacts).

Figure 3A:
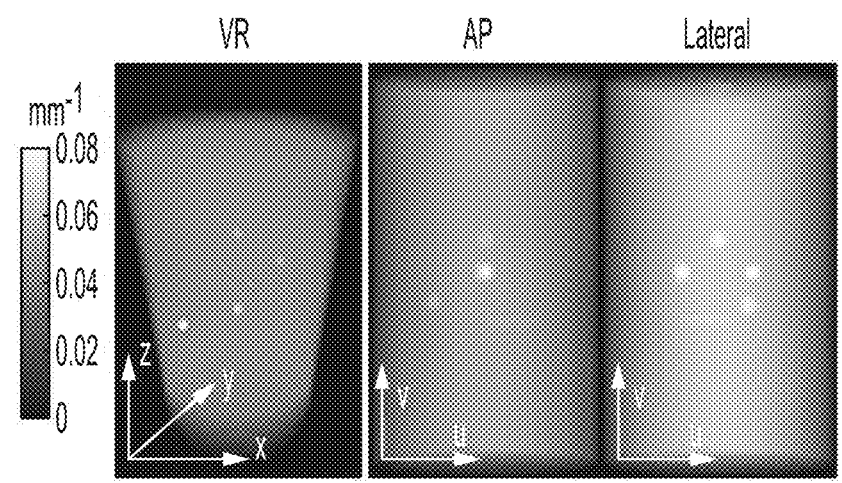
FIGS. 3A-3C show illustrative simulation study of the MAA method.
Figures 3B, 3C:
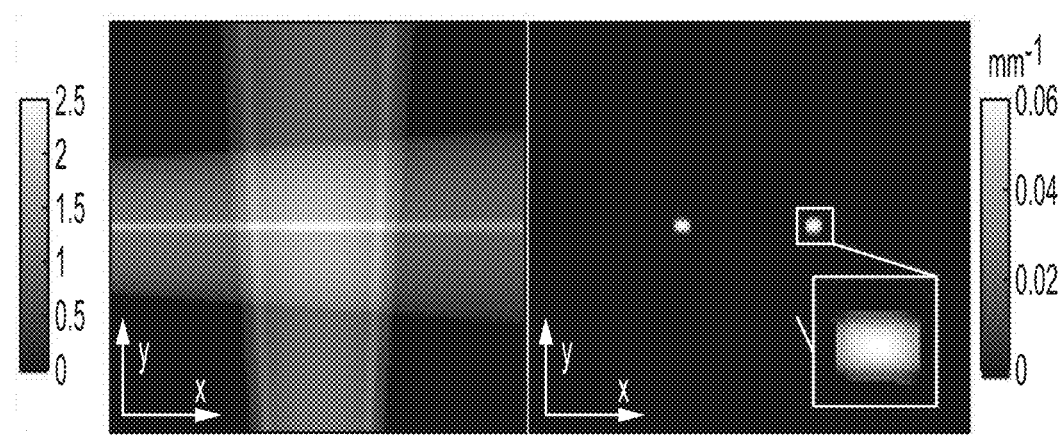

A simulation study was performed to illustrate the disclosed method. The simulation mimics the geometry and x-ray spectrum of the CBCT system shown in FIG. 1A. The digital phantom used in the simulation is a cylinder of water containing several metal spheres and cylindrical rod inserts. FIG. 3A shows a volume rendering of the phantom as well as two labeled scout views (AP and Lateral) of the phantom, corresponding to p(u, v|θ=0, φ=0) and p(u, v|θ=90, φ=0). In this example, two metal spheres overlap in the AP view, which will result in especially low-fidelity projection data in that region and will result in severe metal artifacts in the 3D image reconstruction. FIG. 3B shows the coarse 3D attenuation map formed using a backprojected volume (coarse 3D attenuation map, denoted p) from two scout views. FIG. 3C shows the result of a simple intensity-based segmentation of the attenuation map in FIG. 3B. From the segmented coarse 3D attenuation map ($\mu_{seg}$), a tilted orbit that will avoid metal artifacts as much as possible is computed, as described herein. The dashed-line inset region in FIG. 3C shows a zoomed-in view of one of the segmented regions.

For illustrative purposes using the simulated phantom in FIG. 1A, a calculation of the metric map $q(\theta,\phi)$ is shown below assuming the metal objects are known, i.e., a complete 3D attenuation map of metal objects instead of the segmented coarse 3D attenuation map ($\mu_{seg}$). A more realistic case involving just two views of an unknown phantom (i.e. using seg) is discussed herein.

Figure 4:
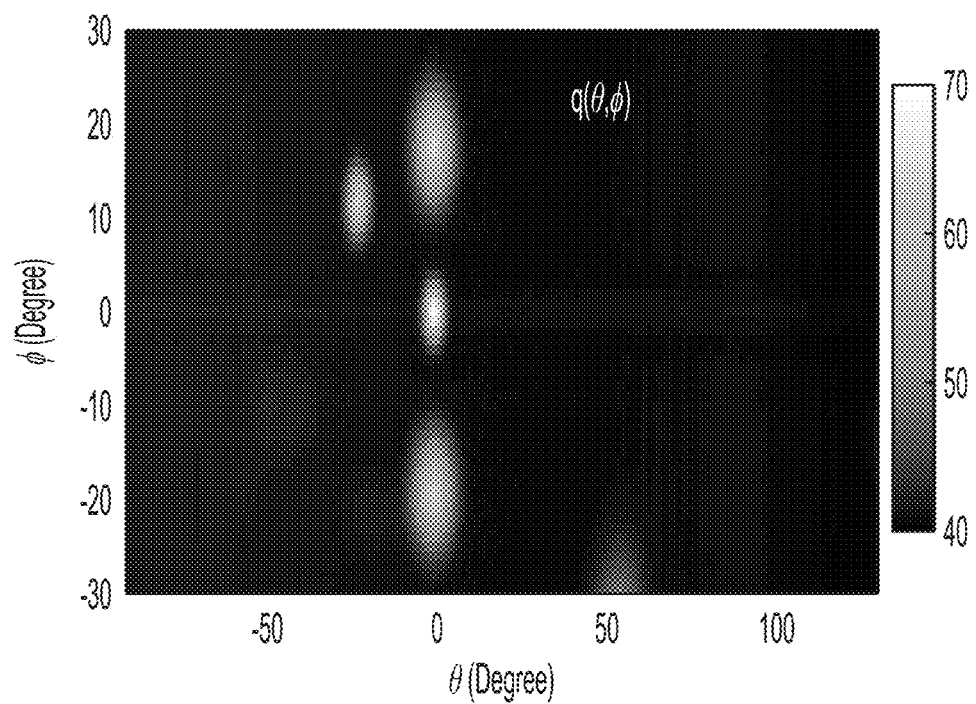
FIG. 4 shows a metric map q($\theta$,$\phi$) computed from views (simulated forward projection) of the complete 3D attenuation map of metal objects. q($\theta$,$\phi$) (signifying the amount of metal related BH artifacts, Eq. (1)) is computed here for all possible C-arm gantry angles and tilts. The result shown here is calculated assuming the metal objects are known perfectly—i.e., the complete 3D attenuation map of metal objects instead of $\mu_{seg}$

A calculation of $q(\theta,\phi)$ according to Equation (1) for the simulated object in FIG. 3 is shown in FIG. 4. One can clearly see the bright regions indicating the θ and φ that will result in severe metal artifacts (low fidelity views) and should therefore be avoided. Note also the simplicity of the MAA solution: namely, desirable source-detector tilt angles are defined simply by horizontal lines (circular trajectory) with lower values in the $q(\theta,\phi)$ map, and some horizontal lines (i.e., some tilt angles) clearly will suffer higher attenuation (metal artifacts) than others. Finding φ* (minimized metal artifacts) for a tilted circular geometry is simply equivalent to finding the horizontal line in the $q(\theta,\phi)$ map that minimizes the objective function, denoted as Q(φ), with respect to the tilt angle φ.

FIG. 4 shows a metric map $q(\theta,\phi)$ computed from views (simulated forward projection) of the complete 3D attenuation map of metal objects. $q(\theta,\phi)$ (signifying the amount of metal related BH artifacts, Eq. (1)) is computed here for all possible C-arm gantry angles and tilts. The result shown here is calculated assuming the metal objects are known perfectly—i.e., the complete 3D attenuation map of metal objects instead of $\mu_{seg}$.

With $q(\theta,\phi)$ ready, one can then calculate objective function Q. This calculation can be divided into the following two scenarios:

$$\underset{\phi(\theta)}{\arg\min} Q(\phi(\theta)) = \sigma[q(\theta, \phi(\theta))] \tag{6}$$

(scenario I): If φ(θ) is constant for all θ: tilted circular orbit (trajectory), corresponds to a horizontal line in FIG. 4, such that every horizontal straight line (from left to right) in FIG. 4 corresponds to a (tilted) circular orbit and every curved line (from left to right) corresponds to a non-circular orbits, for example as shown in FIG. 11.

(scenario II): If φ(θ) is not constant for all θ: non-circular orbit (trajectory), corresponds to a curved line in FIG. 4 (e.g. line 1102 in FIG. 11).

Circular Orbit with Optimal Gantry Tilt: The objective of the equation above can be simplified to the case of finding the tilted (circular/semi-circular) orbit denoted Q(φ). This simplification amounts to finding a "horizontal" row of the $q(\theta,\phi)$ metric map with minimum (or reduced) standard deviation—i.e., a scalar value of φ (φ*) that can be easily solved by exhaustive search of the limited variable space. In practice, there are a number of potential challenges associated with increasingly larger tilt angle, including an increased risk of collision with the operating table and reduced reproducibility in geometric calibration. Therefore, the "optimal" tilt corresponds to a value of φ that is as small as possible, but as large as necessary to avoid or reduce metal artifacts.

Non-Circular Orbit: An increasing number of modern C-arm systems are capable of non-circular orbits—e.g., large fixed-room robotic C-arms (such as the Artis Pheno, Siemens Healthineers) or even the mobile C-arm (Cios Spin 3D) shown in FIG. 1, which provides computer control of θ and φ. This opens the possibility of a full optimization over φ(θ) (i.e., a non-circular orbit) to achieve even lower objective function (Q(φ(θ))) compared to a simple tilted circular orbit (Q(φ)) described above. To reduce the dimensionality of the problem and encourage a smooth and realistic orbit, we modeled φ(θ) as a superposition of cubic b-spline kernels, each centered at one of N=10 knots (at $\theta_i$) equally distributed over the scan arc:

$$\phi(\theta) = \Sigma_{i=0}^{N} f_i B(\theta - \theta_i) \tag{7}$$

where B is a cubic b-spline, $f_i$ is the control parameter for knot i. The optimization in Eq. (7) is generally non-convex and may be challenging to solve with conventional gradient-based methods. An exemplary method by which to solve a minimization of Eq. (7) is the covariance matrix adaptation evolution strategy (CMA-ES) as described by N. Hansen and S. Kern, Evaluating the CMA Evolution Strategy on Multimodal Test Functions, in *Parallel Problem Solving from Nature—PPSN VIII*, edited by X. Yao, E. K. Burke, J. A. Lozano, et al. (Springer Berlin Heidelberg, Berlin, Heidelberg, 2004), pp. 282-291 as a robust solver of Eq. (7) operating in near real-time.

Method 200 continues by computing, at 212, an objective function Q(φ) that is defined with respect to the tilt angle, φ, to capture the overall severity of metal artifacts across all θ. The tilt angle that best avoids metal artifacts (denoted φ*) is then calculated by searching the full range of possible gantry tilts (φ) in order to minimize Q(φ). It is important to note that a strict minimization of Q(φ) may not be necessary. For example, in some scenarios, Q(φ) may be monotonically decreasing with φ (no minimum). In such a case, one should find the value of Q(φ) that is as small as possible, but as large as necessary to avoid metal artifacts. In this sense, selection of the angle φ* is not a true "minimization" or "optimization," but invites important practical considerations (i.e., "as small as possible, but as large as necessary").

An objective function Q(φ) is defined with respect to φ, to capture the overall severity of metal artifacts across all θ. Some example forms of Q(φ) definitions are:

Example 1 (Variation of the Metric Map):

$$Q(\phi) = \sigma_\theta[q(\theta,\phi)] \tag{8}$$

where $\sigma_\theta$ is the standard deviation along θ axis.

Example 2 (Maximum of the Metric Map):

$$Q(\phi) = \max_\theta q(\theta, \phi) \quad (9)$$

where the "max" operator takes the maximum value along θ axis.

Example 3 (Sum of the Metric Map):

$$Q(\phi) = \sum_\theta q(\theta, \phi) \quad (10)$$

where the sum operator is a sum over horizontal lines in the metric map.

Alternative formulations of Q(φ) can also be constructed. Example 1 (e.g. Equation (8)) is one non-limiting example in the MAA solution described here, although there may be situations in which the other Q objectives may be better suited. Using the q(θ,φ) map from FIG. 4, the calculation of Q(φ) using Equation (8) is shown in FIG. 5.

Figure 5:
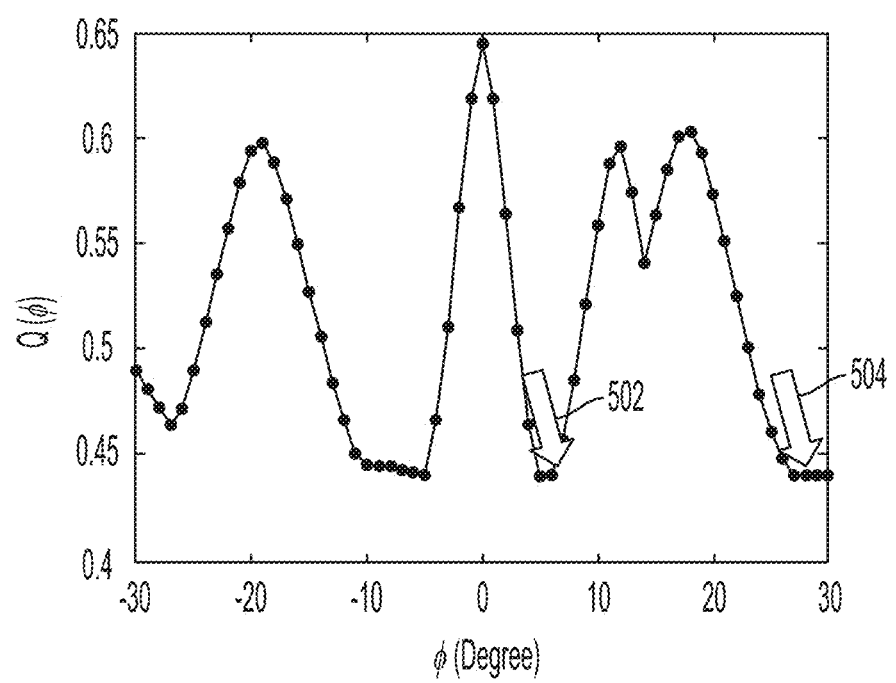
FIG. 5 shows the objective function Q($\phi$) computed from the metric map q($\theta$,$\phi$) in FIG. 4. The form for Q($\phi$) shown here is Eq. (6). The minima in the objective function Q($\phi$) (Q($\phi$)=max q($\theta$,$\phi$)) represent tilt angles ($\phi'$) that best avoid metal artifacts in the 3D image reconstruction (marked by arrows 502 and 504).

FIG. 5 shows the objective function Q(φ) computed from the metric map q(θ,φ) in FIG. 4. The form for Q(φ) shown here is Eq. (8). The minima in the objective function Q(φ) (Q(φ)=max q(θ,φ)) represent tilt angles (φ*) that best avoid metal artifacts in the 3D image reconstruction (marked by arrows 502 and 504).

Method 200 continues by determining, at 214, a tilt angle θ at which to perform the 3D imaging scan: angle φ*. The 3D scan of the patient is performed with the tilted circular trajectory (tilted by φ*). The tilt angle that best avoids metal artifacts (φ*) is calculated by searching the range of possible gantry tilts (φ) in order to minimize Q(φ). For example, a C-arm gantry could commonly provide reliable imaging and geometric calibration over a range in φ from −30° to +30°, which is the range shown in FIG. 5. Note that the exhaustive search over all possible φ is simple and reliable compared to a full iterative optimization, owing to the simplicity of the q(θ,φ) and Q(φ) projection domain formulations. This search of all possible gantry tilts (φ) corresponds simply to considering all horizontal lines in FIG. 4 (metric map q(θ,φ)), and computing Q(φ) for each horizontal line. That is to say, the horizontal line in FIG. 4 that minimizes Q(φ) denotes the desired tilt angle (φ*) for MA.

In FIG. 5, two possible tilt angles that appear to minimize Q(φ) are shown by the arrow 502 at φ~8° and arrow 504 at φ~27°. From the metric map q(θ,φ) in FIG. 4, we see that these angles avoid the low-fidelity views ("bright blobs") associated with the metal spheres and rod in the phantom.

Method 200 can continue by performing, at 216, collision checks of the CT system 102 and/or gantry 104 and performing the 3D imaging scan at the desired tilt angle to obtain a 3D image that avoids the metal artifact.

Figure 6:
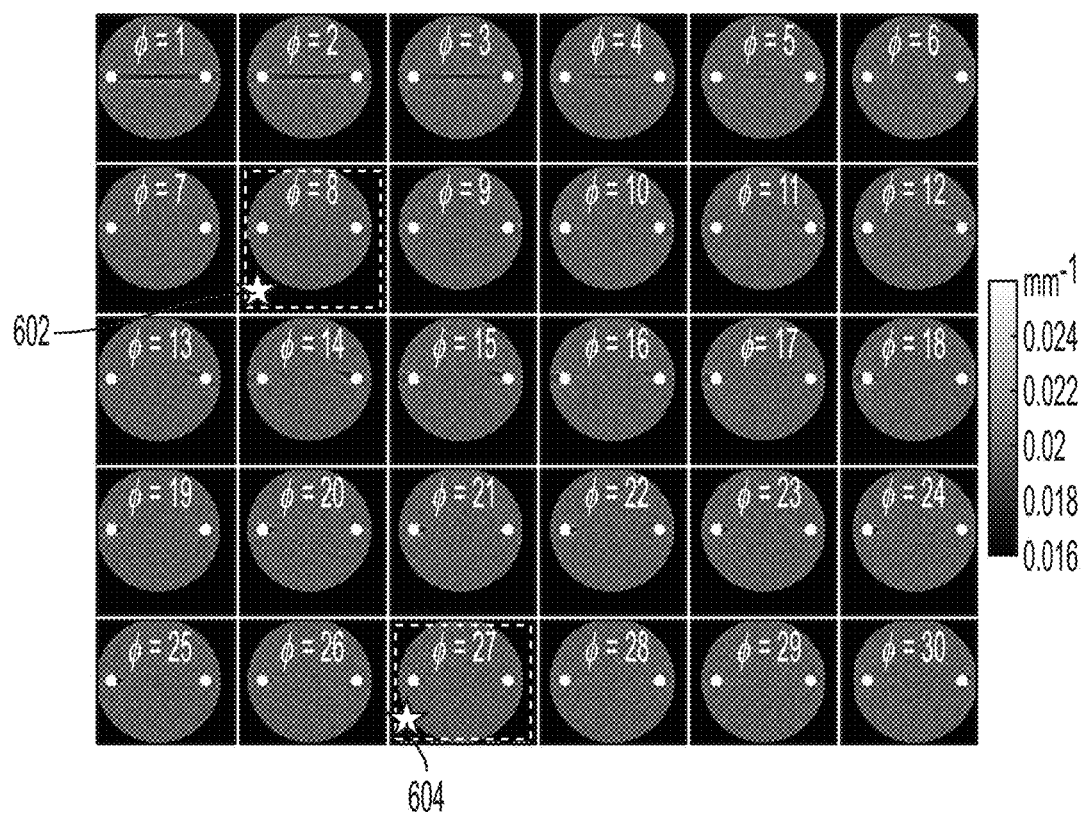
FIG. 6 shows an illustration of the tilt angle that reduces metal artifacts with the MAA method for the simulated phantom in FIG. 3A. 3D image reconstructions at various tilt angle (marked on top of each sub-figure, $\phi$=1-30 degrees) are shown here. The images corresponding to the minima in Q($\phi$) (arrows 502 and 504 in FIG. 5) are marked by stars 602 and 604 for $\phi$=8 and 27 degrees, respectively.

3D image reconstructions (axial slices) for the phantom of FIG. 3A imaged at different tilt angles are shown in FIG. 6. A half range of possible tilt angles are shown, marked at the top of each sub-figure by φ=1°, 2°, ... 30°. The metal artifact associated with two metal spheres in the axial plane is evident as a dark horizontal streak in the images. The metal artifact is severe for tilt angles φ=1°, 2°, .... Note the two images at φ=8° and φ=27° marked by stars 602 and 604, respectively. These tilt angles correspond to the arrows 502 and 504 in FIG. 5 (minima in Q(φ)) that were predicted to avoid the metal artifact. FIG. 6 illustrates that these angles do indeed avoid the metal artifact.

FIG. 6 shows an illustration of the tilt angle that reduces metal artifacts with the MAA method for the simulated phantom in FIG. 3A. 3D image reconstructions at various tilt angle (marked on top of each sub-figure, φ=1-30 degrees) are shown here. The images corresponding to the minima in Q(φ) (arrows 502 and 504 in FIG. 5) are marked by star 602 at φ=8 degrees and star 604 at 27 degrees.

Figure 7A:
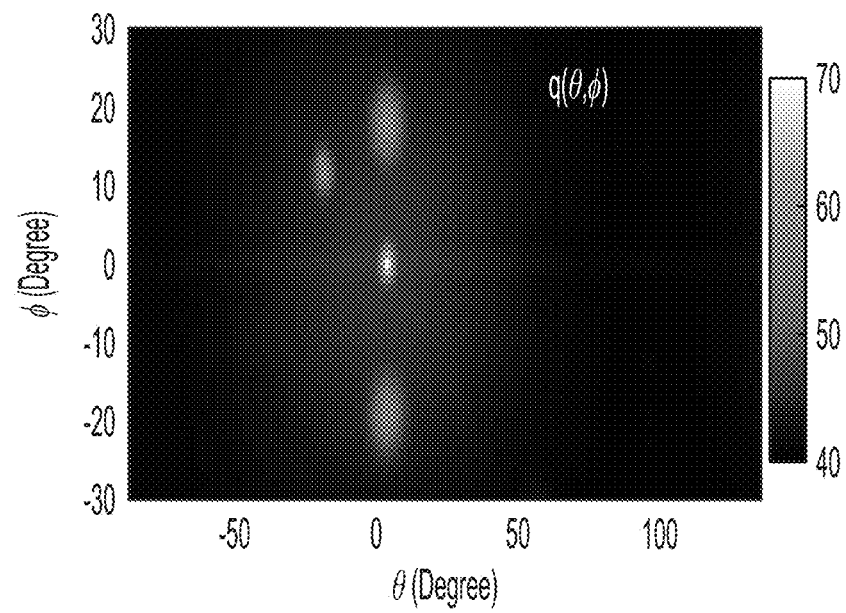
FIGS. 7A and 7B show the MAA metrics computed from just 2 scout projection views.
Figure 7B:
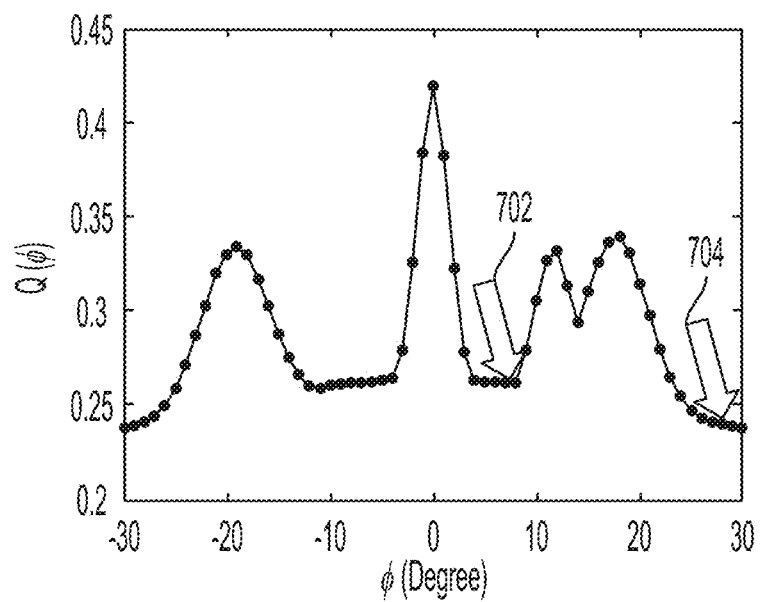

For illustrative purposes, the results of FIG. 4, FIG. 5, and FIG. 6 show the present method in the idealized (unrealistic) scenario in which a complete 3D attenuation map of the metal objects is known. This is simply to give the reader an illustrative understanding of the underlying principles. One non-limiting embodiment accomplishes the same from as few as 2 scout views without knowing the attenuation map of the phantom. FIGS. 7A and 7B show results from 2 scout projection views. First, 2 projection scout views of the phantom are acquired (AP and Lateral views as in FIG. 3A), corresponding to p(u, v|θ=0, φ=0) and p(u, v|θ=90, φ=0). The unweighted backprojection of these 2 scout views forms a coarse 3D attenuation map ($\mu_c$) as shown in FIG. 3B. This coarse 3D attenuation map is then segmented via simple intensity-thresholding as shown in FIG. 3C, corresponding to $\mu_{seg}$. For the example phantom, this results in the localization (not the exact shape) of two strongly attenuating metal objects.

The metric map q(θ,φ) is then determined by forward projecting $\mu_{seg}$. The result is shown in FIG. 7A. Note again the bright blobs corresponding to views at which strong attenuation and metal artifacts can be expected. Note also the difference between FIG. 7A and FIG. 4: the metric map q(θ,φ) from FIG. 7A is computed from just 2 scout views (from $\mu_{seg}$), whereas the metric map q(θ,φ) of FIG. 4 was from a full knowledge of metal objects within the digital phantom (complete 3D attenuation map of the metal objects). Despite having just 2 views from which to estimate $\mu_{seg}$, the method properly identifies projection views associated with strong metal artifacts.

The objective function Q(φ) can then be determined from the metric map q(θ,φ) as shown in FIG. 7B. Here again, note the differences between the Q(φ) objective in FIG. 7B and that in FIG. 5. The objective in FIG. 7B was computed based on just 2 scout views, but it properly identifies the desirable tilt angles at ~φ=8° and ~φ=27°. Those metrics (q(θ,φ) and Q(φ)) determined with $\mu_{seg}$ (shown in FIG. 7) are relatively consistent with those determined with the complete 3D attenuation map of the metal objects (shown in FIG. 4 and FIG. 5), showing the feasibility of only using two scout views to determine the required tilt angle.

FIGS. 7A and 7B show the MAA metrics computed from just 2 scout projection views. FIG. 7A show the metric map q(θ,φ). Note similarity to FIG. 4 (which computed the metric map assuming complete 3D attenuation map of the metal objects). The metric map computed from just 2 views still manages to localize views corresponding to high attenuation that will result in metal artifacts. FIG. 7B shows the objective function Q(φ) computed from horizontal lines in the metric map of FIG. 7A. This again reproduces the idealized results of FIG. 5, showing desirable tilt angles at ~φ=8° and ~φ=27° (arrows 502 and 504, respectively).

Figures 9A, 9B, 9C:
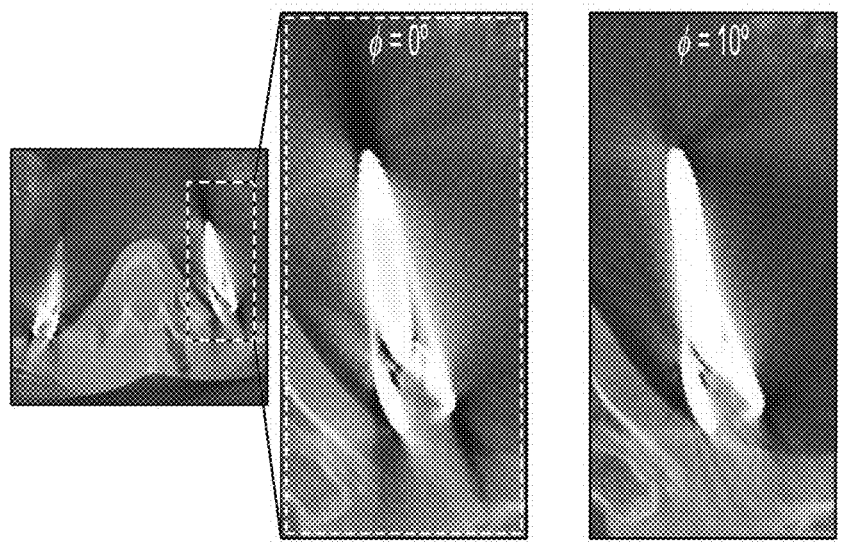
FIGS. 9A-9F show axial views of the chest phantom acquired with different tilt angle. Note the artifacts (bright and dark streaks about the spine screw) for $\phi$=0°, compared to the reduction of such artifacts for images acquired at the tilt angle $\phi$=20 or 30° predicted by the MAA method.
Figures 9D, 9E, 9F:
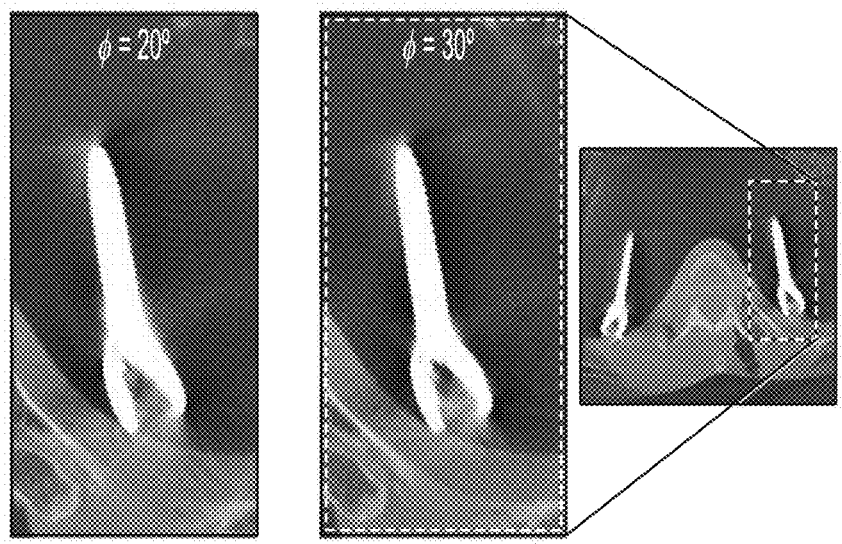

The present method was further tested with a physical phantom experiment using the CBCT system with a mobile C-Arm shown in FIG. 1A. As shown in FIG. 9, an anthropomorphic chest phantom involving two bilateral pedicle screws placed near the spine was used in this study.

Figure 8A:
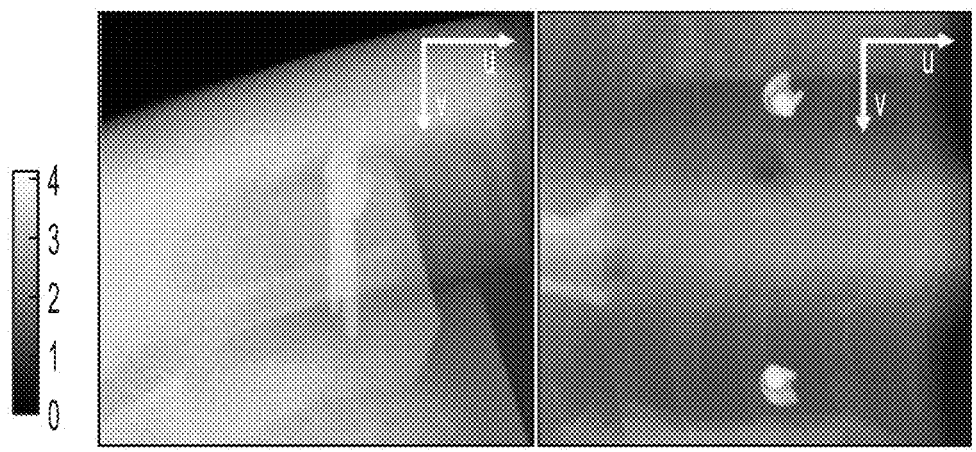
FIGS. 8A-8E show physical phantom experiment results for the MAA method.

Two scout projection views of the phantom were acquired—illustrated in FIG. 8A, corresponding to p(u, v|θ=0, φ=0) and p(u, v|θ=90, φ=0). A coarse 3D attenuation map [$\mu_c$, FIG. 8B] is then determined by (unweighted) backprojection of the two scout views FIG. 8A, which is then segmented by intensity thresholding to yield the segmented coarse 3D attenuation map ($\mu_{seg}$) in FIG. 8C.

The metric map $q(\theta,\phi)$ is computed (using Eq. (1)) by forward projecting $\mu_{seg}(c)$ as explained above, giving the map in FIG. 8D. Note the bright blob in the center of the metric map about $\theta \cdot 100°$ and $\phi$ from −15 to 15°. This implies almost any tilt angles ($\phi > \sim 15°$ or $< \sim -15°$) will avoid metal artifact for this phantom to a large extent.

Figures 8B, 8C:
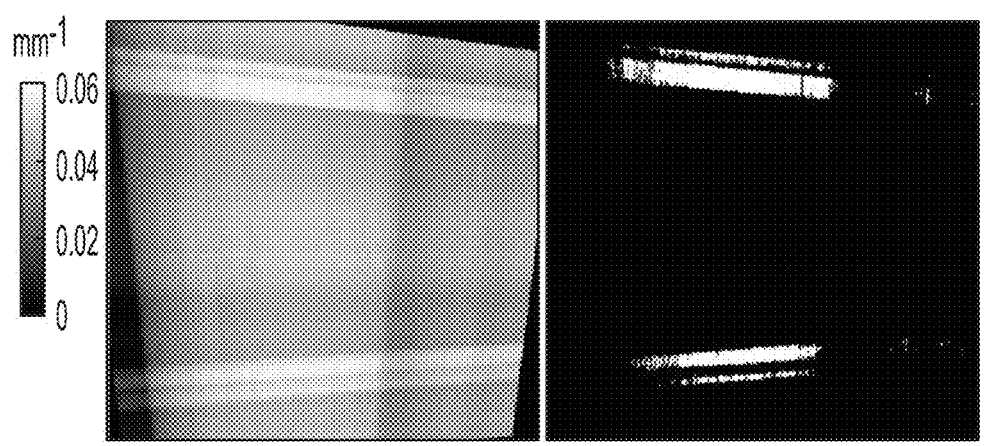
Figure 8D:
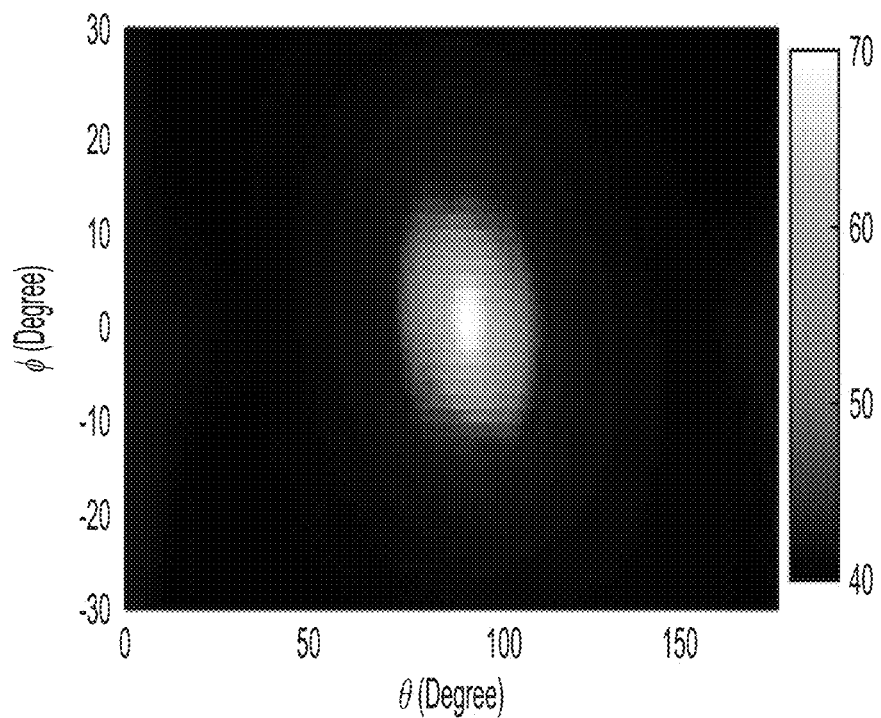
Figure 8E:
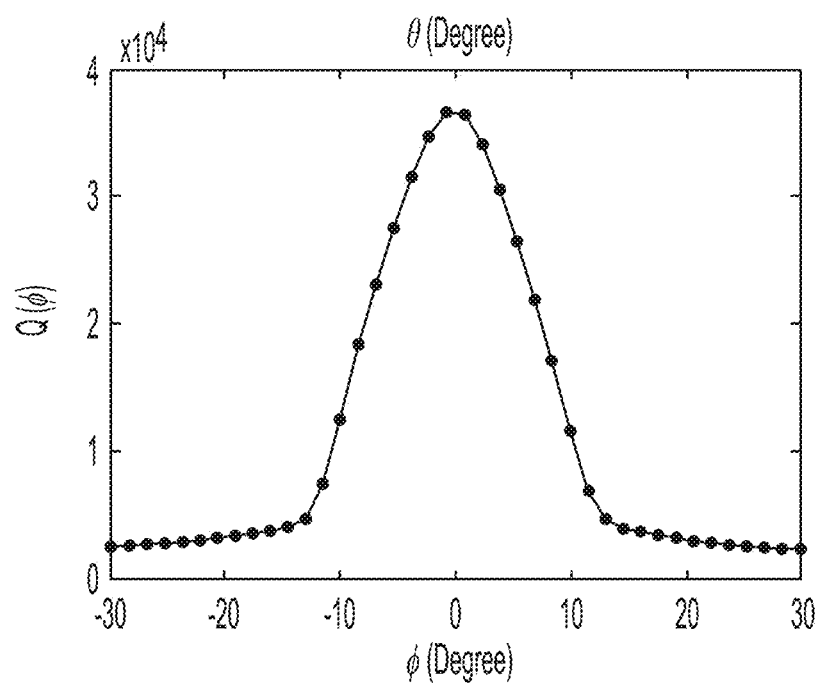

The objective function $Q(\phi)$ is computed from metric map $q(\theta,\phi)$ in (d), yielding the function shown in FIG. 8E. The broad spike near $\phi \sim 0°$ marks a range in gantry tilt that should clearly be avoided. In fact, this scenario illustrates the common problem with imaging at $\phi = 0°$, which would suffer major metal artifact. Minima in $Q(\phi)$ (alternatively, very low values in $Q(\phi)$ relative to the peak value) identify desirable tilt angles ($\phi^*$).

3D image reconstructions of the phantom are shown in FIGS. 9A-9F for $\phi$ from −30° to 30°. One can see that when $\phi$ is close to 0° (the conventional case), the phantom suffers from strong metal artifacts—dark band at the tip of the screw and the "blooming" at the edge of the screw. Whereas when a tilt angle larger than +15° or −15° is used (=30° for example), the metal artifacts are reduced as desired, enabling much better delineation of the screw boundary. This observation matches the $\phi$ optimization results from FIGS. 8D and 8E.

FIGS. 8A-8E show physical phantom experiment results for the MAA method. FIG. 8A shows two projection scout views, $p(u, v|\theta=0, \phi=0)$ and $p(u, v|\theta=90, \phi=0)$. FIG. 8B shows a coarse 3D attenuation map ($\mu_c$) formed by unweighted backprojection of the two scout views in FIG. 8A. FIG. 8C shows intensity-based segmentation of the coarse 3D attenuation map ($\mu_{seg}$). FIG. 8D shows the metric map $q(\theta,\phi)$ computed using Eq. (1) by forward projection of FIG. 8C ($\mu_{seg}$). FIG. 8E shows the objective function $Q(\phi)$ computed from horizontal lines in FIG. 8D, the minimum in which suggests tilt angles ($\phi^*$) that will avoid metal artifacts.

FIGS. 9A-9F show axial views of the chest phantom acquired with different tilt angle. Note the artifacts (bright and dark streaks about the spine screw) for $\phi=0°$, compared to the avoidance of such artifacts for images acquired at the tilt angle $\phi=20$ or 30° predicted by the present method.

The 3D image is reconstructed using well established methods. Since the orbit is circular, the 3D image can be formed by common 3D filtered backprojection methods. Alternatively, the 3D image can be reconstructed by iterative MBIR, which may improve overall signal-to-noise properties, as common with MBIR. Optionally, the 3D image can be reconstructed with processing of the projection data and/or image reconstruction via various PMAC methods to further suppress metal artifacts. Other artifact corrections (e.g., x-ray scatter, lag, or motion artifacts) can also be optionally applied as typical in the state of the art. The 3D image reconstruction and processing chain is relatively unchanged. An important consideration, of course, is that the system geometry underlying the 3D image reconstruction process must account for the gantry tilt; for example, the geometric calibration of the system must account for the gantry tilt.

Thus, a source-detector trajectory (viz., tilted circular orbit) is determined that avoids metal artifacts prior to the actual 3D scan. Metal artifacts are thereby avoided without the need for prior information or modification to the reconstruction and artifact correction image processing pipeline.

Figure 10A:
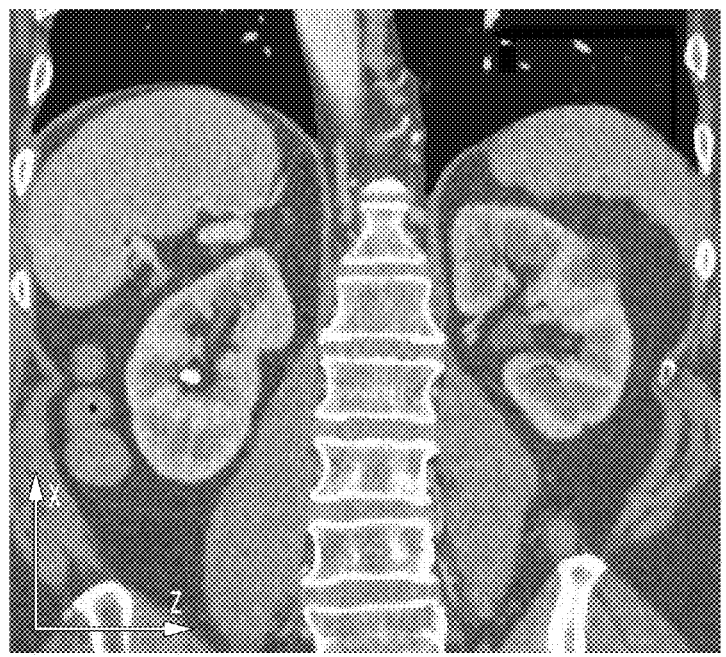
FIG. 10A shows a coronal image of the simulation phantom #2.
Figure 10B:
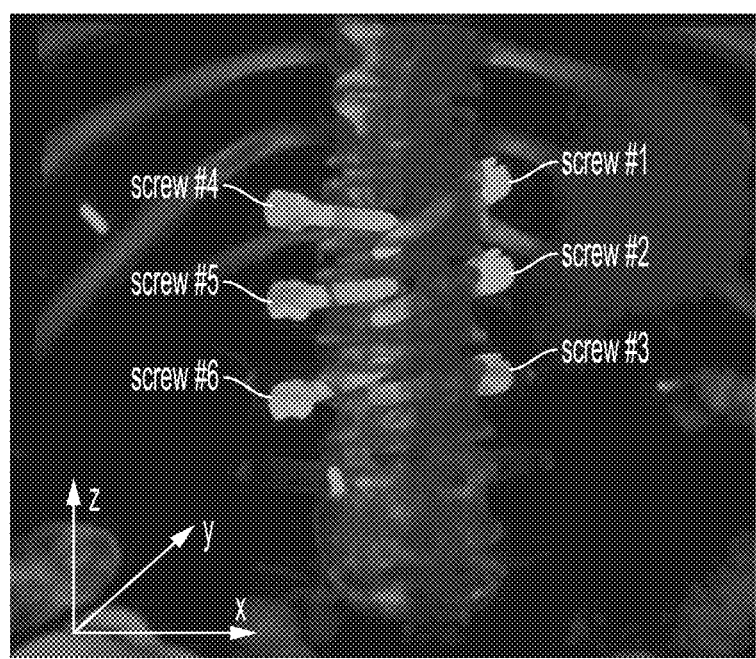
FIG. 10B shows a volume render of the simulation phantom #2 (with screws shown).

A second simulation study extended the MAA approach to a scenario of more realistic anatomy and metallic instrumentation with a non-circular orbit. FIG. 10A shows a coronal image of the simulation phantom #2. FIG. 10B shows a volume render of the simulation phantom #2. As shown in FIGS. 10A and 10B, Experiment #2 simulated the anatomy of a human chest (drawn from the cancer image archive (TCIA) dataset) implanted with three pairs of bilateral spinal pedicle screws (out-of-plane with respect to the central axial plane by −22°, −11°, 0° on one side of the spine, and 0°, +11°, and +22° on the other side of the spine) and labeled #1-6, respectively. To add a degree of complexity, the attenuation of screws #1-3 was increased by 10% compared to screws #4-6. We extend the orbit optimization to non-circular orbits. We analyzed the degree to which the non-circular orbit reduced metal artifact compared to the optimal tilted circular orbit in terms of visual image quality and RMSE from ground truth.

Figure 11A:
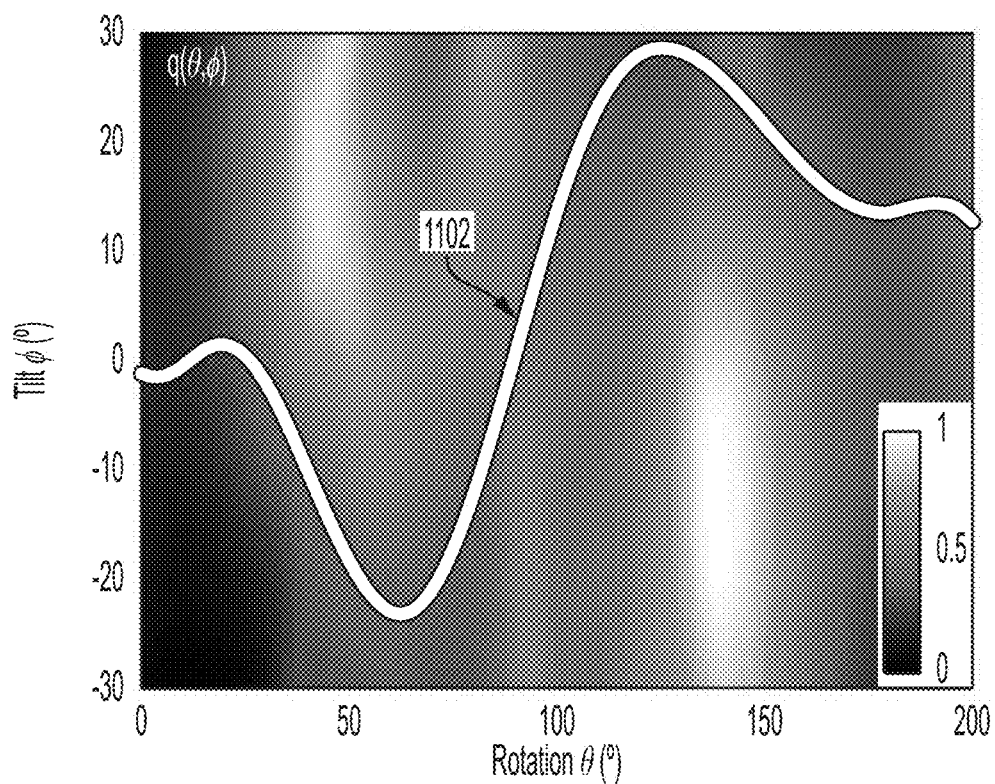
FIG. 11A shows the q($\theta$,$\phi$) metric map computed from the simulation phantom #2. The optimal non-circular orbit is marked by curve 1102.
Figure 11B:
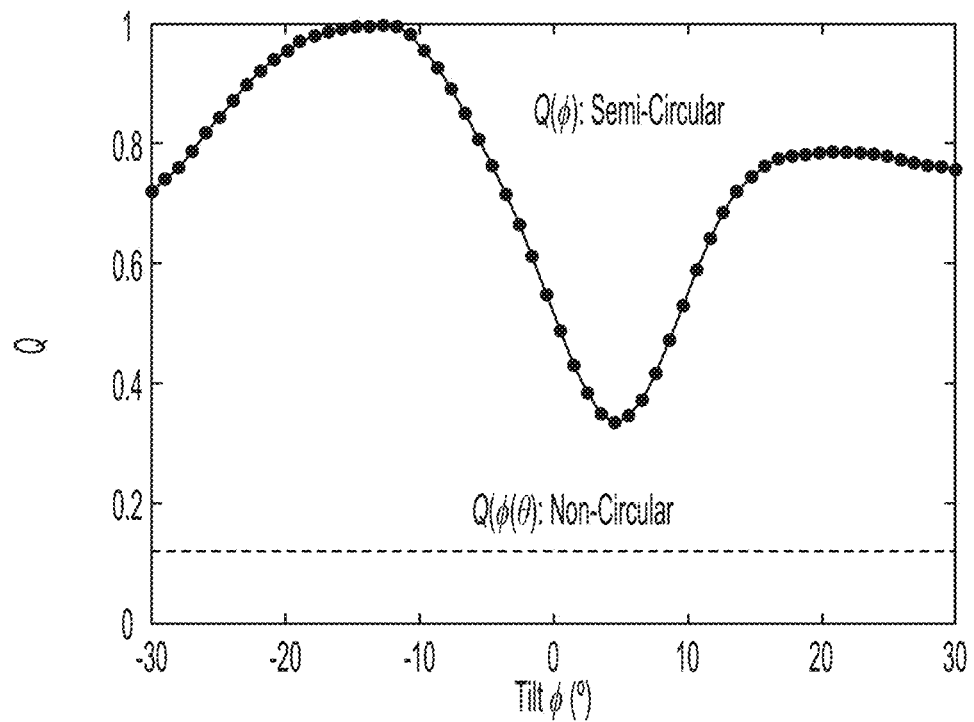
FIG. 11B shows the Q($\phi$) (semi-circular) objective plotted over a range of gantry tilt angles. The non-circular Q($\phi$($\theta$)) achieves a lower value than any setting of semi-circular orbit.
Figure 11C:
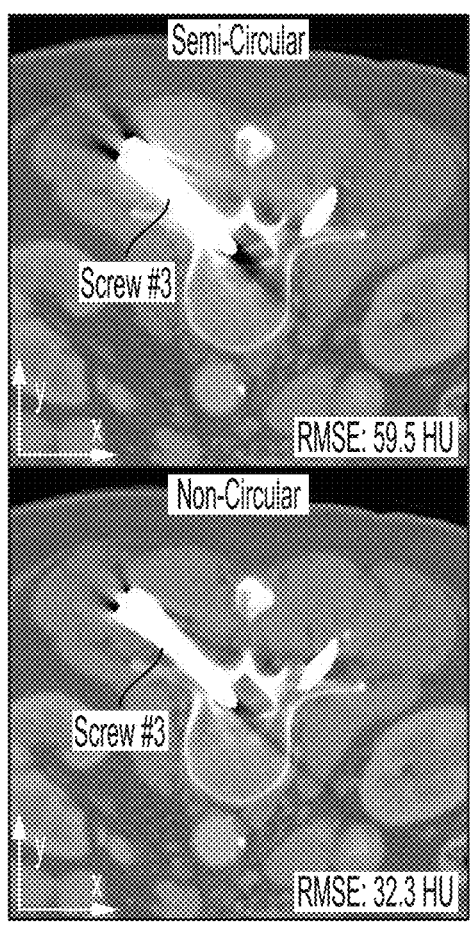
FIG. 11C shows axial slices (screw #3, out-of-plane angle 0°) imaged with optimal circular (top) and non-circular (bottom) orbit (reconstructed with penalized weighted least square (PWLS) method).
Figure 11D:
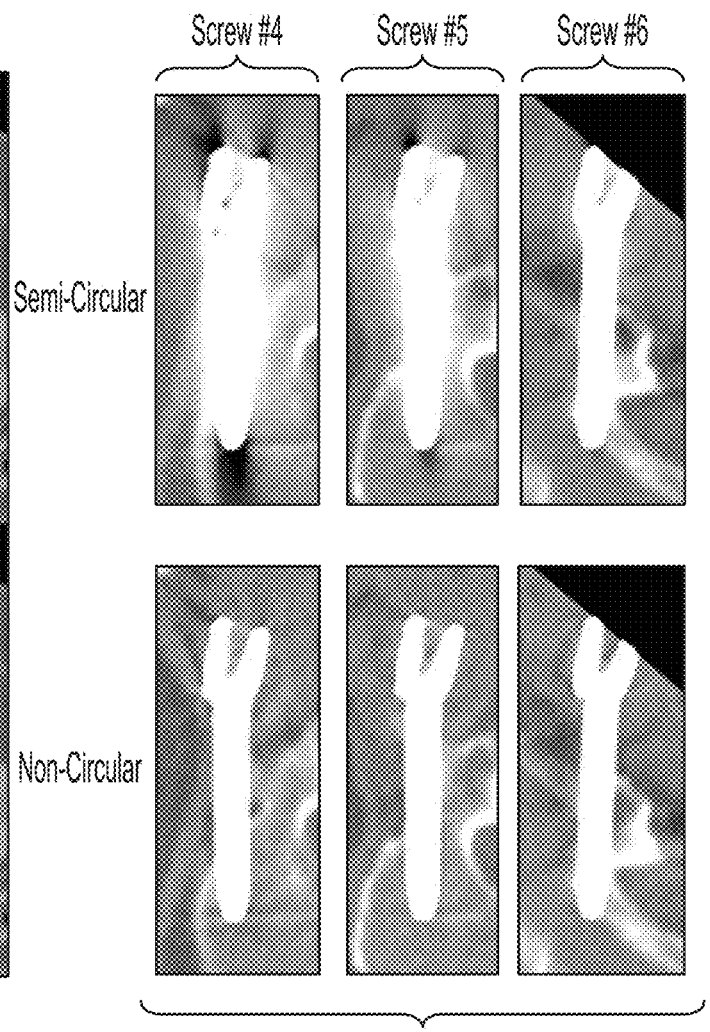
FIG. 11D shows three example screws (#4-6, out-of-plane angle 0°, 11°, 22° respectively) acquired with optimal semi-circular (top) and non-circular (bottom) orbit, noting that the images obtained using the non-circular MAA method exhibit significantly reduced metal artifact. Tilted axial views across the shaft of each screw were shown.
Figure 11E:
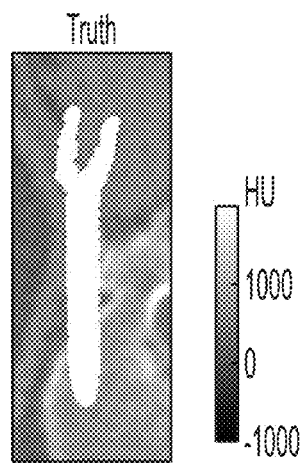
FIG. 11E shows ground truth axial image of the simulated screw.

FIGS. 11A-11E show result of the simulation #2: Simulation of realistic anatomy and screws for MAA prediction of optimal non-circular orbit. In particular, FIG. 11A shows the $q(\theta,\phi)$ metric map. The optimal non-circular orbit is marked in green. FIG. 11B shows the $Q(\phi)$ (semi-circular) objective plotted over a range of gantry tilt angles. The non-circular $Q(\phi(\theta))$ achieves a lower value than any setting of semi-circular orbit. FIG. 11C shows axial slices (screw #3, out-of-plane angle 0°) imaged with optimal circular (top) and non-circular (bottom) orbit (reconstructed with penalized weighted least square (PWLS) method). FIG. 11D shows three example screws (#4-6, out-of-plane angle $\theta$, 11, 22° respectively) acquired with optimal semi-circular (top) and non-circular (bottom) orbit. Tilted axial views across the shaft of each screw were shown. FIG. 11E shows ground truth axial image of the simulated screw.

Result for this simulation: FIGS. 11A-11E shows the $q(\theta,\phi)$ metric map computed for the simulated spine phantom. Note the two bright regions corresponding to low-fidelity views (strong metal-induced bias) through the screw shaft. The optimal tilted semi-circular orbit based on $Q(\phi)$ suggests a tilt angle of 4%, which avoids some of the low-fidelity views, but not all of them, as shown in the image of FIG. 11C, which exhibits fairly strong residual metal artifacts (though still an improvement over the non-tilted orbit, not shown for brevity). Note that $Q(\phi)$ is an objective for the overall metal artifact arising from all screws evident in the projection data; therefore, while a larger tilt angle (e.g., $\phi=-20°$) might reduce the artifact associated with screw #3 (out-of-plane angle: $\phi$, FIG. 11C), it would result in increased metal artifacts for other screws like screw #1 and #2 (out-of-plane angle: −22°, −11° respectively). For this case, therefore, there is no single gantry tilt that substantially reduces the artifact for all screws.

This issue was resolved by extension of the MAA approach to non-circular orbit optimization. The optimal non-circular orbit (marked by curve 1102 overlaid in FIG. 11A) avoided most of the low-fidelity views and as shown in FIG. 11B, resulted in a much lower $Q(\phi(\theta))$ characteristic compared to the optimal circular orbit. The optimal non-circular MAA orbit achieved a strong reduction in metal artifact for all screws—evident in the lower image of FIG. 11C and the panels in FIG. 11D. While some residual artifacts are still evident (especially for screw #1-3 whose attenuation are higher), the MAA orbit reduced overall RMSE by ~46%, confirming the effectiveness of MAA method for definition of non-circular orbits.

Figure 12:
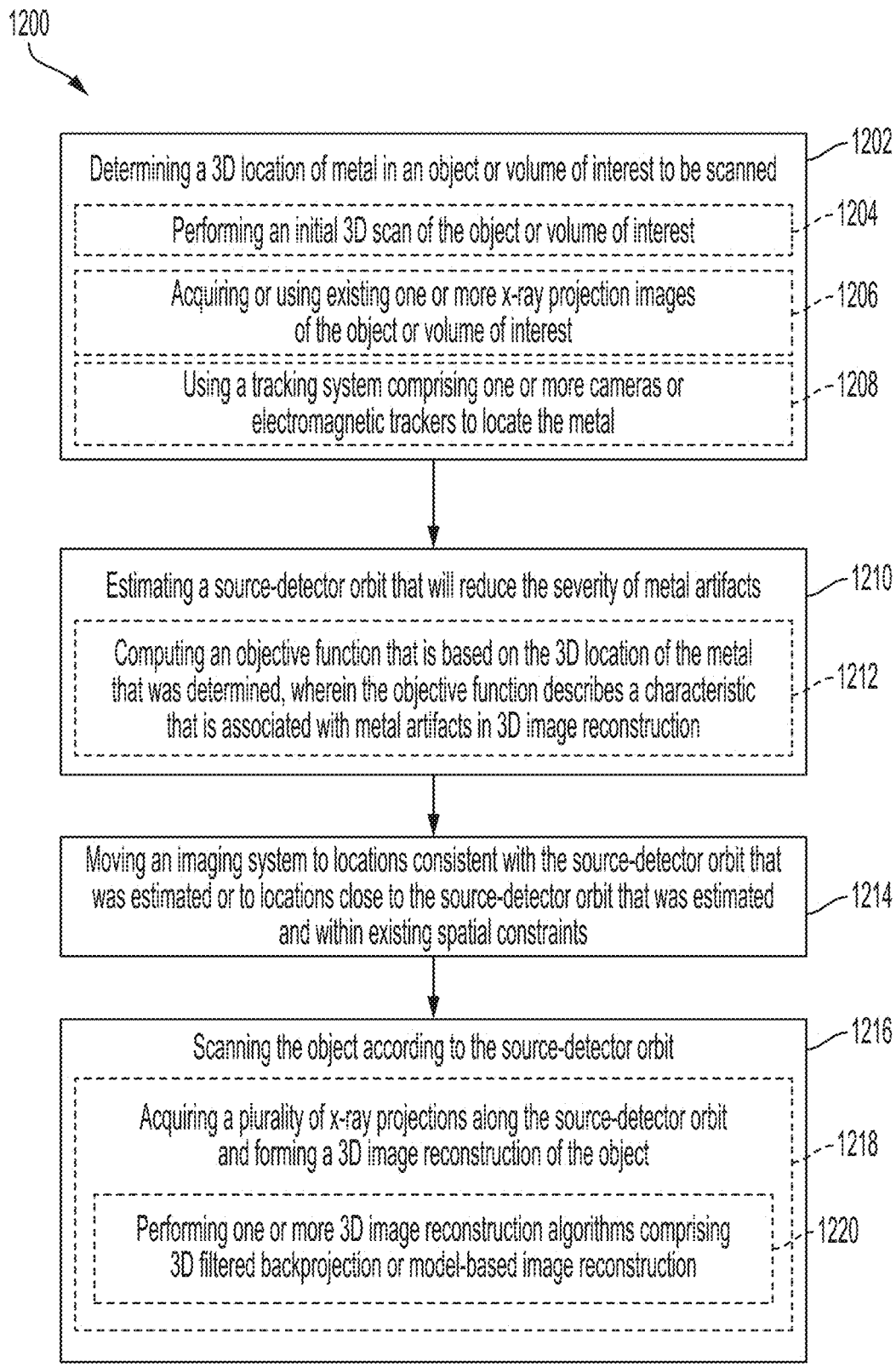
FIG. 12 shows method for metal artifact avoidance in 3D x-ray imaging, according to examples of the present disclosure.

FIG. 12 shows method 1200 for metal artifact avoidance in 3D x-ray imaging, according to examples of the present disclosure. Method 1200 begins by determining, at 1202, a 3D location of metal in an object or volume of interest to be scanned. The determining, at 1204, can further comprise one or more of the following: performing, at 1204, an initial 3D scan of the object or volume of interest, acquiring, at 1206, one or more x-ray projection images of the object or volume of interest, using one or more previously acquired x-ray images, or using a tracking system, at 1208, comprising one or more cameras or electromagnetic trackers to locate the metal.

Method 1200 continues by estimating, at 1210, a source-detector orbit that will reduce the severity of metal artifacts. The source-detector orbit comprises a position and orientation of an x-ray source and a detector for projections to be acquired in the in 3D x-ray imaging. The severity of metal artifacts is reduced compared to a circular path in a plane perpendicular to a long axis of the object. The estimating, at 1210, the source-detector orbit can further comprise computing, at 1212, an objective function that is based on the 3D location of the metal that was determined. The objective function describes a characteristic that is associated with metal artifacts in 3D image reconstruction. For example, the characteristic can comprise an estimation of a spectral shift or an attenuation.

Method 1200 continues by moving, at 1214, an imaging system to locations consistent with the source-detector orbit that was estimated or to locations close to the source-detector orbit that was estimated and within existing spatial constraints. The moving, at 1214, can be based on constraints of the imaging system (for example, electrical or mechanical limits), and location of the volume of interest (such that the resulting 3D image will contain the volume of interest). The source-detector orbit that was estimated can be adjusted as necessary for consistency with such factors and constraints. For example, if the spatial constraints of the imaging system are such that the determined source-detector orbit cannot be used, then source-detector orbits that are close to those that are determined can be used. The source-detector orbits that are considered close can be, for example, within a few degrees in tilt angle ($\phi$), such as within less than 1°, between about 1° and 3°, between 1° and 5°, between about 1° and 7°, between about 1° and 10°, where the ranges are includes of the limits of the ranges.

Method 1200 continues by scanning, at 1216, the object according to the source-detector orbit. The scanning, at 1216, can further comprise acquiring, at 1218, a plurality of x-ray projections along the source-detector orbit and forming, at 1220, a 3D image reconstruction of the object. The forming, at 1220, the 3D image reconstruction can further comprise performing, at 1222, one or more 3D image reconstruction algorithms comprising 3D filtered backprojection or model-based image reconstruction.

In summary, the present MAA method accurately predicted tilted circular and/or non-circular orbits that reduced the magnitude of metal artifacts in CBCT reconstructions. The method was able to localize complex distributions of metal instrumentations with 2-6 low-dose scout projections acquired during routine pre-scan collision check. A simple U-Net segmentation was found to be sufficient in localizing (segmenting) metal objects in sparse views even in complex anatomical scenes and to generalize well to a range of metal objects without manufacturer-specific device models. Simulations showed MAA orbits to reduce RMSE in 3D image reconstructions by ~46-70% and "blooming" artifacts (FWHM of the screw shaft) by ~20-45%. Non-circular orbits defined by MAA achieved ~46% reduction in RMSE compared to the optimal circular orbit. MAA method was shown to accurately predict tilted circular/non-circular orbits that minimize metal artifacts in all experiments.

Additionally and/or alternatively to the above description, the capacity for 3D imaging with non-circular orbits on a mobile C-arm with motorized tilt and angulation of the gantry is further described. Specifically, the issues of geometric calibration for general (not pre-defined) non-circular orbits is addressed and evaluate 3D imaging performance characteristics of non-circular orbits compared to conventional circular orbits. The capability to extend the MAA method to non-circular orbits is used to minimize metal-induced bias. The method is shown to operate well with just two low-dose scout views (without other prior information of patient anatomy/metal objects) and is compatible with MAR and polyenergetic reconstruction methods that can further improve image quality.

Figure 13A:
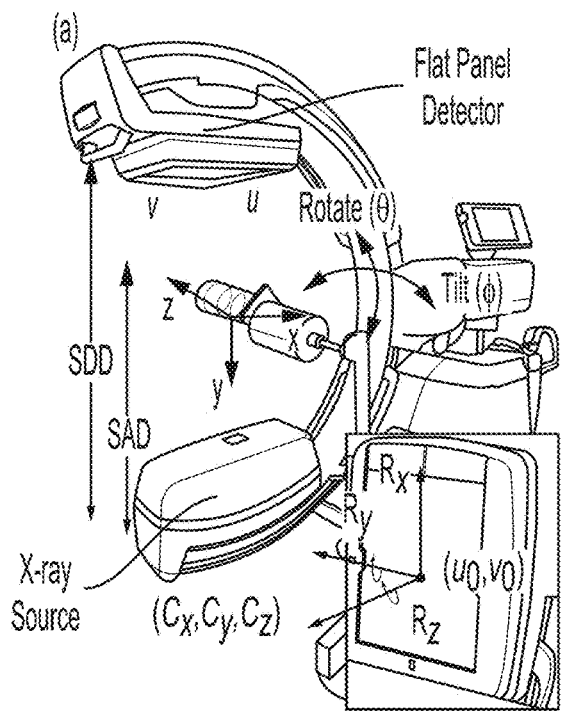
FIGS. 13A and 13B shows a mobile C-arm, C-arm geometric parameters and zoomed-in view of the detector, respectively, according to examples of the present disclosure. The nine parameters (degrees-of-freedom) determined via geometric calibration are marked. (B) Source-detector orbits illustrated on a sphere. Circular orbits are shown (various settings of gantry tilt, $\phi$). An example non-circular orbit is shown ($\phi$ changing with $\theta$). The zoomed inset illustrates estimation of geometric parameterization for one view determined by interpolation of four nearest vertices in a library of geometric calibrations of circular scans.

The mobile C-arm used in this disclosure (Cios Spin 3D, Siemens Healthineers, Forcheim, Germany) is shown in FIG. 13A. The C-arm has motorized control of rotation angle ($\theta$: 0° to 196°) and gantry tilt ($\phi$: −30° to 30°, due to realistic considerations of patient/table collision), permitting non-circular orbits to be executed by variation of $\theta$ and $\phi$ during the scan. Tilted circular orbits (constant $\phi$) can be calibrated using established methods. However, for non-circular scan trajectories defined by methods like "task-driven" imaging and MAA, the orbit is designed on the fly and may not be amenable to a previously acquired calibration given the large variety of feasible ($\theta,\phi$) combinations. An interpolation-based approach is used to address this issue, detailed as follows.

Alternatively, rather than solving the image reconstruction with a system geometry determined by the conventional geometric calibration method or the interpolated geometric calibration method, the image reconstruction could be solved with a system geometry determined by the "self-calibration" approach of Self-calibration of cone-beam CT geometry using 3D-2D image registration S Ouadah, J W Stayman, G J Gang, T Ehtiati and J H Siewerdsen Published 10 Mar. 2016 © 2016 Institute of Physics and Engineering in MedicinePhysics in Medicine & Biology, Volume 61, Number 7 and Hopkins IP case C13072 Patent: Pub. No.: US 2017/0238897 A1.

Figure 13B:
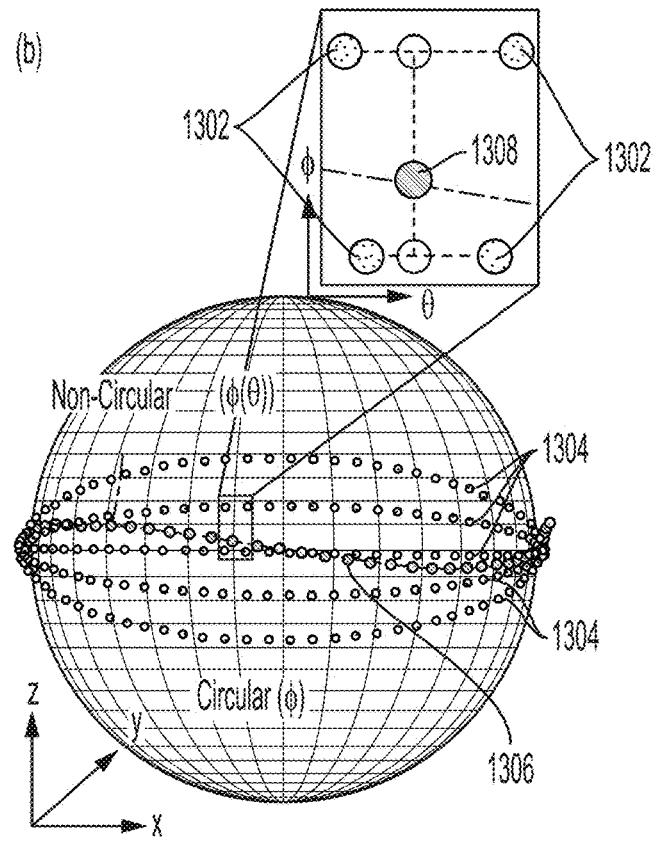

FIGS. 13A and 13B shows a mobile C-arm, C-arm geometric parameters and zoomed-in view of the detector, respectively, according to examples of the present disclosure. FIG. 13A is similar to the mobile C-arm of FIG. 1A. The nine parameters (degrees-of-freedom) determined via geometric calibration are marked by dots 1302. FIG. 13B shows source-detector orbits illustrated on a sphere. Circular orbits are in shown by curves 1304 (various settings of gantry tilt, $\phi$). An example non-circular orbit is shown in curve 1306 ($\phi$ changing with $\theta$). The zoomed inset illustrates estimation of geometric parameterization for one view (dot 1308) determined by interpolation of four nearest vertices in a library of geometric calibrations of circular scans (dots 1302).

First, a library of geometric calibrations is built for circular obits with tilt ranging from $\phi$=−30° to +30° at 5° intervals using a cylindrical BB phantom placed at the same tilt angle as the C-arm gantry. Affine transformation of the library registers all calibrations into a common coordinate system (co-registration):

$$P_{\phi=0} = P_{\phi=\phi^*} \times T_{tilt} \times T_w \tag{11}$$

-continued $$T_{tilt} = \begin{bmatrix} 1 & 0 & 0 & 0 \\ 0 & \cos(\phi^*) & -\sin(\phi^*) & 0 \\ 0 & \sin(\phi^*) & \cos(\phi^*) & 0 \\ 0 & 0 & 0 & 1 \end{bmatrix} \quad (12)$$

$$T_w = \begin{bmatrix} 1 & 0 & 0 & t_x \\ 0 & 1 & 0 & t_y \\ 0 & 0 & r_z & t_z \\ 0 & 0 & 0 & 1 \end{bmatrix} \quad (13)$$

where $P_{\phi=\phi^*}$ is the projection matrix at tilt angle $\phi^*$, and $T_{tilt}$ is a transformation through tilt angle $\phi^*$ (read from the C-arm motor encoder). The transformation $T_w$ accounts for small discrepancies in displacement (t) and tilt ($r_z$) between the BB phantom and the gantry in each member of the library, determined by 3D-3D registration. This co-registration step: (i) makes sure that the orientation of the reconstructed image remains unchanged regardless of the orbit; (ii) improves the accuracy of the interpolation step below.

The co-registered calibrations were then decomposed into nine parameters: SDD (source detector distance), C (source location, in x, y, z), $u_0$, $v_0$ (piercing point), and R (detector rotation matrix, in x, y, z) as shown in dots 1302 in FIG. 13A. The system geometry for a general non-circular orbit can then be estimated by interpolating the geometric parameters from the calibration library—viz., the four nearest views from calibrated tilted circular orbits as illustrated in FIG. 13B. Parameters SDD, $u_0$ and $v_0$ were estimated by scattered linear interpolation, and C, R by spherical linear interpolation (slerp). The slerp operation is non-commutative and was performed first in θ and then in φ for reduced interpolation error, since the θ direction is more finely sampled in the calibration library.

Given two scout views, the MAA method determines a binary 3D reconstruction (coarse segmentation, $\mu_{seg}$) describing the 3D location of metal objects in the FOV. Unlike in MAR, a coarse segmentation was found to be sufficient for MAA, requiring only an approximation of the shape, size, and orientation of metal objects (cf. MAR methods that typically require very accurate segmentation to avoid introducing secondary artifacts).

Coarse segmentation used an end-to-end convolutional neural network (CNN), as discussed above, which learns features simultaneously in projection and image domains. Specifically, projection domain feature extraction layers are connected to image domain 3D segmentation layers through a frozen (no learnable parameters) backprojection layer. Intuition underlying such a network is that image domain segmentation is improved by fusing shape information from the projection domain (before being smeared by backprojection), and projection domain feature extraction is guided by the segmentation loss backpropagated from the image domain.

Figure 14:
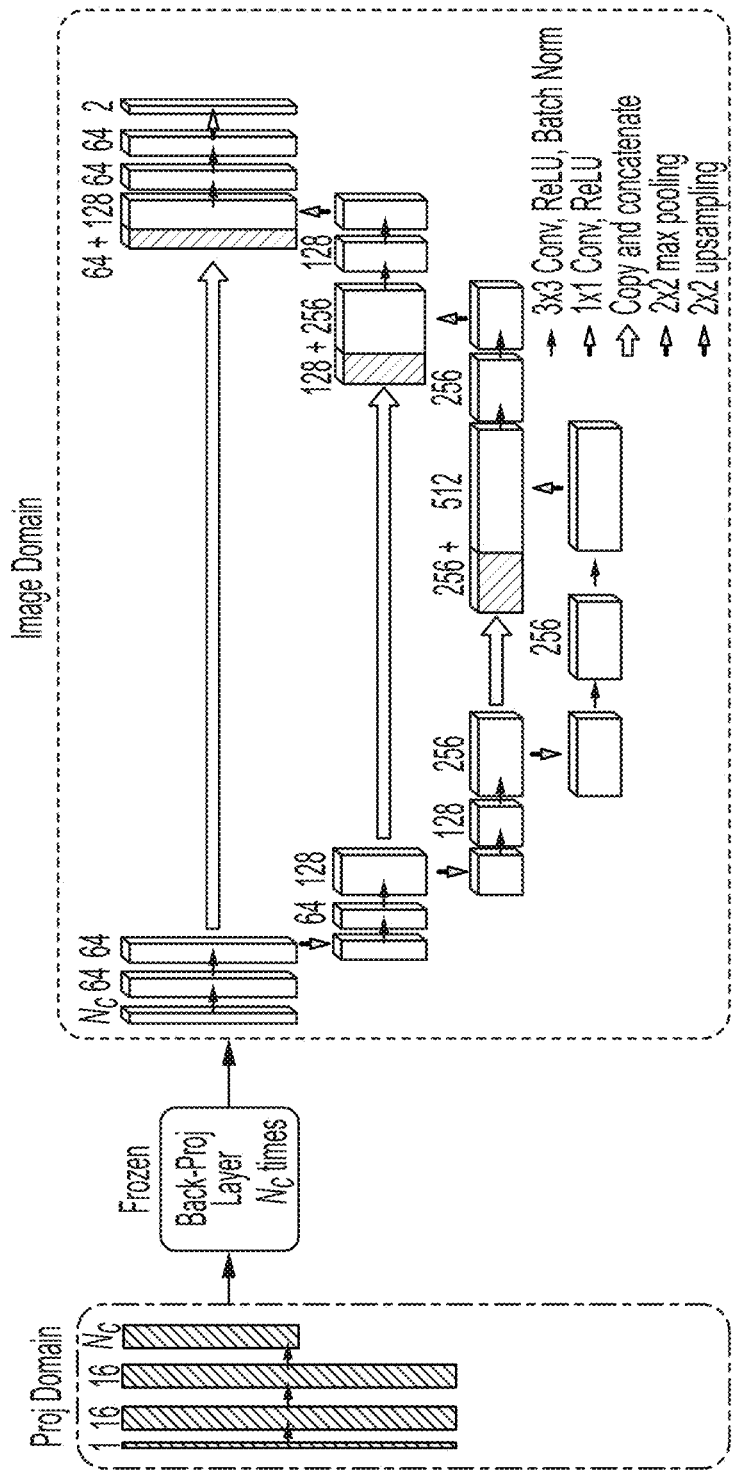
FIG. 14 shows an end-to-end neural network for 3D localization/segmentation of metal instrumentation according to examples of the present disclosure.

FIG. 14 shows an end-to-end neural network for 3D localization/segmentation of metal instrumentation according to examples of the present disclosure. Projection domain feature extraction layers are connected to the image domain segmentation layers through a frozen backprojection layer (determined from C-arm geometry), enabling joint learning in projection and image domains.

Each projection domain feature extraction layer contains two 3×3 convolutions, each followed by a rectified linear unit (ReLU) with batch normalization, and in the end a 2×2 max pooling layer. The 3D segmentation layers were implemented as a three-layer multi-channel 3D U-Net (detailed in FIG. 14) with general Dice coefficient as loss function. At the beginning of the 3D segmentation layers, the derivative of the loss function with respect to the input of the backprojection layer is the forward projection operation (determined with C-arm geometry and Siddon ray tracing, not taken as learnable parameter of the network), enabling joint learning in projection and image domains. The network was "He normal" initialized and trained using the Adam optimizer with an initial learning rate of 5×10-4 for 100 epochs.

One of the key hyper-parameters of the network is the number of feature maps extracted in the projection domain (denoted as Nc as shown in FIG. 14), which is also the number of input channels for the multi-channel 3D U-Net in the image domain. The backprojection step (within the backprojection layer) is performed individually for each channel.

For simplicity and to avoid the requirement for vendor-specific metal instrument models, the network was trained with only simulated data, which was generated from 10 abdominal and thoracic CT images drawn from the Cancer Imaging Archive (TCIA) and a random number of generic metal objects: ellipsoids ranging in size and eccentricity (10-80 mm major and minor axes) and coarsely segmented spine screws drawn from CT images. Future work could certainly involve adding higher fidelity object models (e.g., vendor-specific designs) and other application-specific objects (e.g., fracture fixation plates) for improved performance. The effects of data truncation, beam hardening (through poly-energetic forward projection), scatter, lag, glare, and noise (quantum and electronic) were included in DRR generation. Data augmentation included variation in the location, size, orientation, aspect ratio, and attenuation of simulated metal objects in each DRR, resulting in a total of ~8,400 (8,000 training+400 validation) images.

The results from an experimental study are provided below. First, geometric calibration of non-circular orbits are discussed. The reproducibility of geometric parameters was evaluated for an example non-circular orbit (φ linearly increasing from −20° to +20° while θ linearly increasing from 0° to 196°) by repeating the geometric calibration (not interpolation) 4 times over an 8-hour period of normal use. Three scenarios were evaluated: (i) a conventional pre-calibrated circular orbit (denoted as "Calibrated Circular"); (ii) a pre-determined and pre-calibrated non-circular orbit (denoted as "Calibrated Non-Circular"); and (iii) a general non-circular orbit for which the projection matrix is determined by the interpolation-based method described above (denoted as "Interpolated Non-Circular"). Basic image quality characteristics of scans under these three scenarios were evaluated in terms of spatial resolution (modulation transfer function, MTF) and 3D sampling characteristics (cone-beam artifacts) in a head phantom containing a variety of custom inserts. The axial plane MTF was determined from the edge-spread function measured from a high-contrast (~300 HU) cylindrical rod insert. The magnitude of cone-beam artifacts was measured in terms of the full-width-at-half-maximum (FWHM) of the superior-inferior edges of flat disks ("Defrise phantom") inserted within the cranium. All scans involved 400 projections over a 196° arc in θ at 110 kV, 1.65 mAs/view, with a 30 s scan time.

Next, the metal artifact avoidance (MAA) with non-circular orbits is discussed. The performance of the CNN-based metal object localization step was evaluated in terms of Dice coefficient in the validation dataset and in the testing dataset [scans of a cadaver instrumented with six pairs of pedicle screws (Nuvasive, San Diego USA)]. The performance of the proposed end-to-end method was compared with two other methods: (i) conventional image domain U-Net segmentation on direct backprojection of scout views (referred to as the "single U-Net"); [5] and (ii) projection domain U-Net segmentation of metal objects, followed by backprojection and image domain U-Net segmentation (referred to as the "dual U-Net"). Note that the two U-Nets in (ii) were trained separately (not end-to-end).

The performance of the MAA method was evaluated in a phantom study involving an anthropomorphic chest phantom containing a natural human skeleton in tissue-equivalent plastic and 8 spinal pedicle screws (DePuy-Synthes, Raynham USA; ranging 30-60 mm in length). The screws were placed with out-of-plane angle ranging from −20° to +30° (positive on one side of the spine, negative on the other). Metal artifact magnitude was assessed in terms of "blooming" about the shaft of the screw (FWHM of the screw minus its true width) for conventional circular orbit scans and the optimal non-circular orbit defined by MAA.

The results of the study for geometric calibration of non-circular orbits are now discussed. FIG. 15A and FIG. 15B show reproducibility of geometric parameters for the pre-determined non-circular orbit described above, where FIG. 15A shows a location of the piecing point $(u_0, v_0)$ and FIG. 15B shows SDD in $\phi$ repeat trials over an 8-hour interval of routine use. A reduction in reproducibility was observed: for example, the standard deviation in piercing point location $(u_0, v_0)$ over repeat trials was ~1.7 mm (vs. ~0.8 mm for a conventional circular orbit). Note that the mobile C-arm was not electromechanically tuned beyond its standard clinical deployment, which does not support non-circular orbits in standard use. As shown below, however, despite the reduced mechanical reproducibility, the interpolation-based calibration provided a reasonable estimate of system geometry supporting 3D image reconstruction.

Figure 16A:
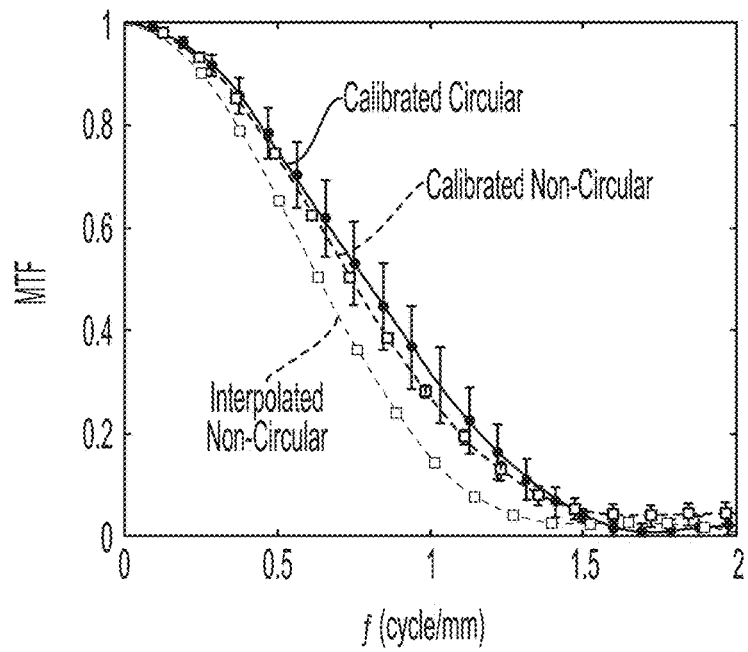
FIG. 16A-FIG. 16D show the effect of geometric calibration accuracy on spatial resolution (modulation transfer function, denoted MTF) and 3D image quality, where
Figures 16B, 16C, 16D:
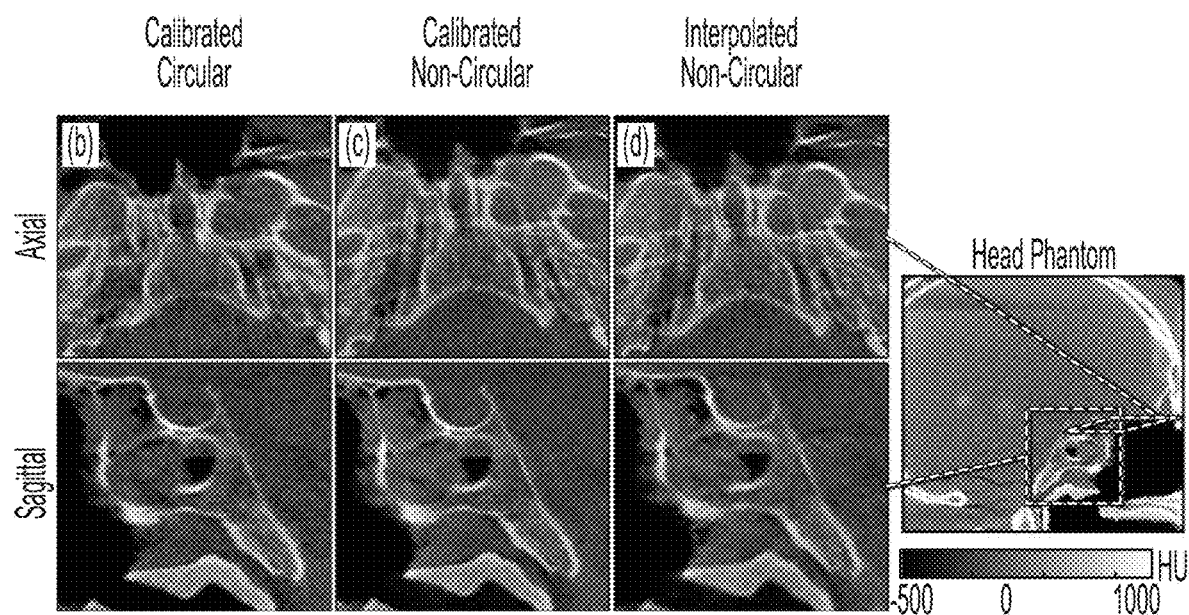

FIG. 16A-FIG. 16D illustrate how errors in geometric calibration relate to reduction in spatial resolution for the three scenarios defined above, where FIG. 16A shows MTF for the three scenarios defined by the arranged in FIG. 13A and FIG. 13B and FIG. 16B, FIG. 16C, and FIG. 16D shows axial and sagittal zoomed-in views (skull-base) of a head phantom for the three scenarios, respectively. Compared to the standard "Calibrated Circular" scenario, the "Calibrated Non-Circular" scenario showed minor reduction in MTF (3.5% reduction in the spatial frequency at which MTF=0.10, denoted as $f_{10}$) due to the decreased reproducibility in calibration parameters. The "Interpolated Non-Circular" scenario showed further reduction in resolution (~12% reduction in $f_{10}$) due to two effects: smoothing of geometric parameters in the interpolation; and ignoring differences in gantry momentum for a continuous non-circular orbit compared to the discrete library of circular scans. Despite the reduction in MTF, images obtained with the "Interpolated Non-Circular" scenario appear visually comparable to the others, as in FIG. 16B and FIG. 16C. Therefore, the interpolation-based method appears to provide a reasonable estimate of system geometry for non-circular scans for which neither a pre-calibration nor a "self-calibration" (using previous scan and 3D-2D registration) is available.

Figures 17A, 17B, 17C:
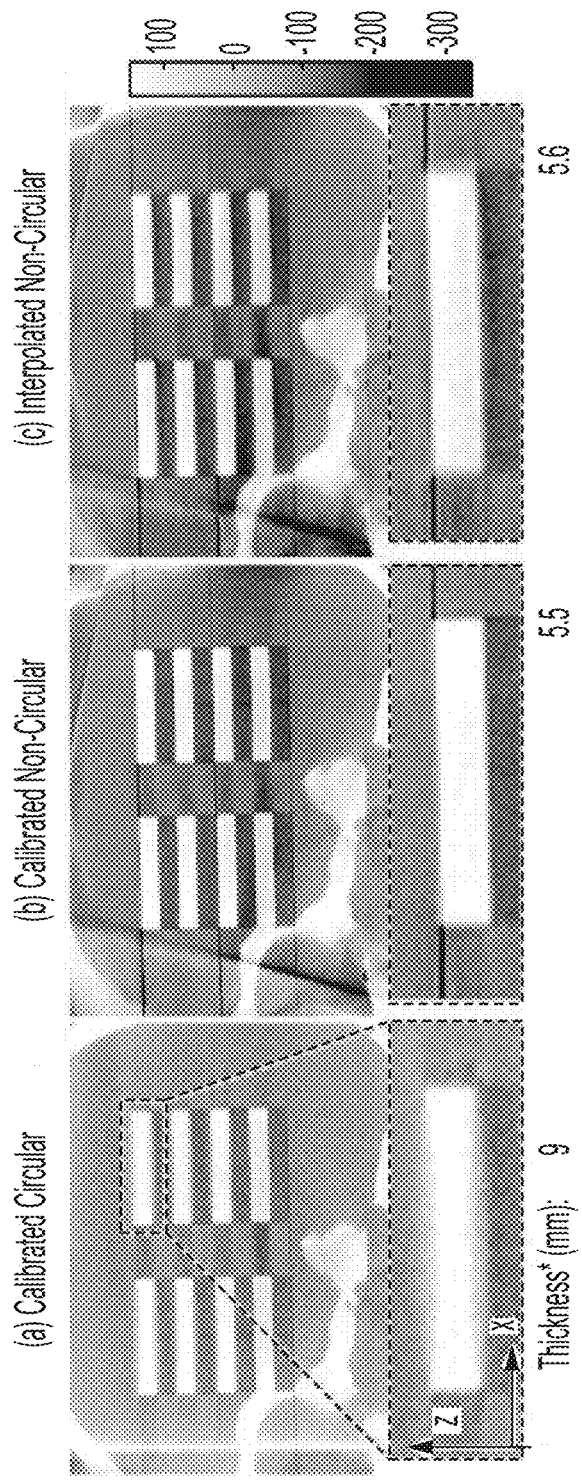
FIG. 17A, FIG. 17B, and FIG. 17C show the expected reduction in cone-beam artifacts from non-circular orbits in sagittal images of a head phantom containing stacks of flat disks as defined by the arrangement of FIG. 13A and FIG. 13B. The apparent thickness (full-width-at-half-maximum, denoted FWHM) of the edge of the uppermost disk was reduced from 9 mm for the standard "Circular Protocol" to its true thickness (~5.5 mm) for both of the non-circular scenarios.

FIG. 17A-FIG. 17C show the expected reduction in cone-beam artifacts from non-circular orbits in sagittal images of a head phantom containing stacks of flat disks as defined by the arrangement of FIG. 13A and FIG. 13B, where FIG. 17A is for a calibrated circular orbit, FIG. 17B is for a calibrated non-circular orbit, and FIG. 17C is for an interpolated non-circular orbit. The apparent thickness (FWHM) of the uppermost disk was reduced from 9 mm for the standard "Circular Protocol" to its true thickness (~5.5 mm) for both of the non-circular scenarios.

The results of the study for MAA with Non-Circular Orbits are now discussed. FIG. 18 shows performance of segmenting real or simulated metal implants in terms of Dice Coefficient (denoted DC) in validation testing of three network types (single U-Net, dual U-Net, and End-to-End) as a function of the number of projection views, illustrating improved segmentation performance of the end-to-end network compared to the single and dual U-Nets. The increase in DC (especially for fewer scout views) confirms the effectiveness of end-to-end training: for just two scout views, the end-to-end method increased Dice by ~29% in the validation dataset, and by ~42% in the testing dataset compared to the dual U-Net. This is consistent with other works in literature that utilizes end-to-end training.

Figures 19A, 19B, 19C, 19D, 19E:
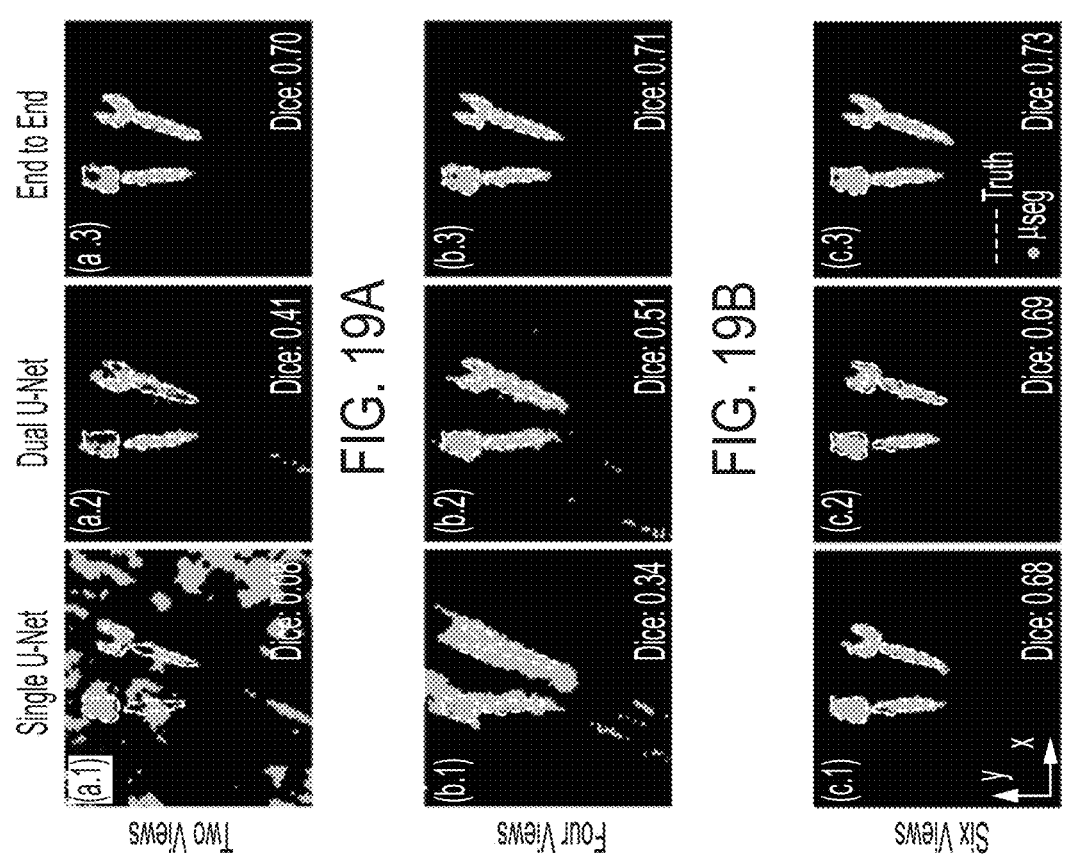
FIG. 19A-FIG. 19E shows segmentation performance of three neural networks in the testing dataset (cadaver with 12 pedicle screws) according to examples of the present disclosure.
Figure 20A:
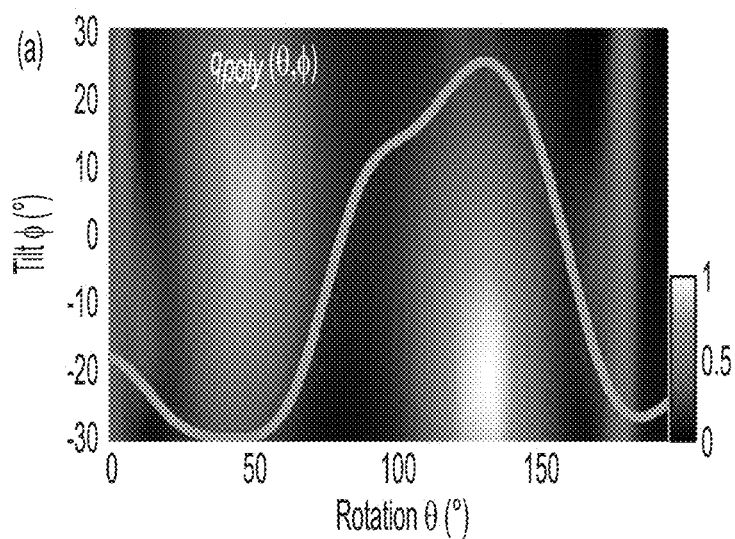
Figure 20B:
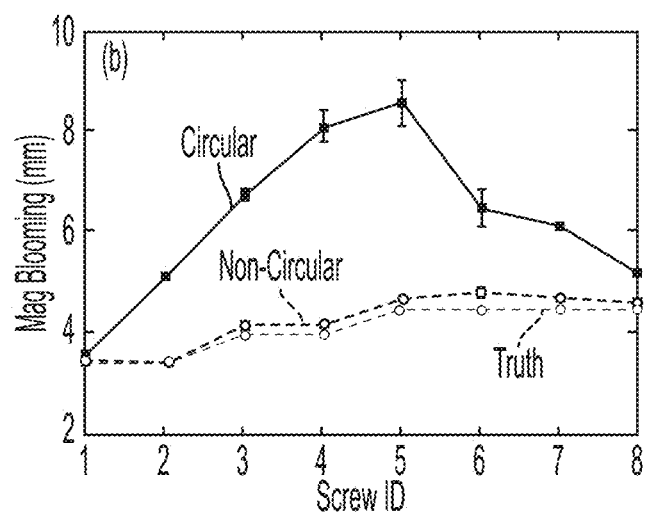

FIG. 19A-FIG. 19E show segmentation performance of three neural networks in the testing dataset (cadaver with 12 pedicle screws). FIG. 19A-FIG. 19C show example axial slice segmentation overlaid with ground truth. Segmentations are shown for varying number of scout views. FIG. 19D shows isosurface of $\mu_{seg}$ computed from two views for the end-to-end method. FIG. 19E shows isosurface of ground truth segmentation (downsampled the same as $\mu_{seg}$).

FIG. 20A-FIG. 20F show the $q(\theta,\phi)$ metric map computed by the MAA method with just two scout views of the chest phantom and spine screws. Clearly, there is no circular orbit [horizontal line in (a)] that would substantially reduce metal artifact for all screws, as there is always at least one region of strong metal-induced bias in the $(\theta,\phi)$ trajectory space (roughly corresponds to the out-of-plane angle of the screw). This issue is resolved by 2D minimization of Eqs. (6) and-(7), resulting in the non-circular orbit marked by the cyan curve (a). The non-circular orbit avoids most of the low-fidelity views, steering a path in $(\theta,\phi)$ that minimizes variation in spectral shift. The resulting image quality is shown in FIGS. 20C-FIG. 20F, showing strong reduction in blooming artifacts about the screw (~70% improvement in screw shaft blooming achieved with the optimal non-circular orbit).

In summary, a method for geometric calibration of non-circular C-arm CBCT orbits is described, giving a practical means to estimate system geometry from a discrete library of circular scan calibrations. Although the geometric calibration method carried a measurable reduction in MTF, the effect on visual image quality was relatively minor. CBCT images acquired from non-circular orbits were shown to improve 3D sampling characteristics (e.g., reduction of cone-beam artifacts), as expected. Such capability enabled a method (called MAA) that identifies non-circular orbits with minimal metal-induced biases. An end-to-end neural network is described to localize metal objects from just two scout views without strong prior information of the patient anatomy or metal instruments. Integration of the end-to-end network with the MAA method for non-circular orbits demonstrated strong reduction in metal artifacts in phantom and cadaver studies. Moreover, the method is compatible with established MAR and polyenergetic reconstruction algorithms to further reduce artifacts.

Figure 23:
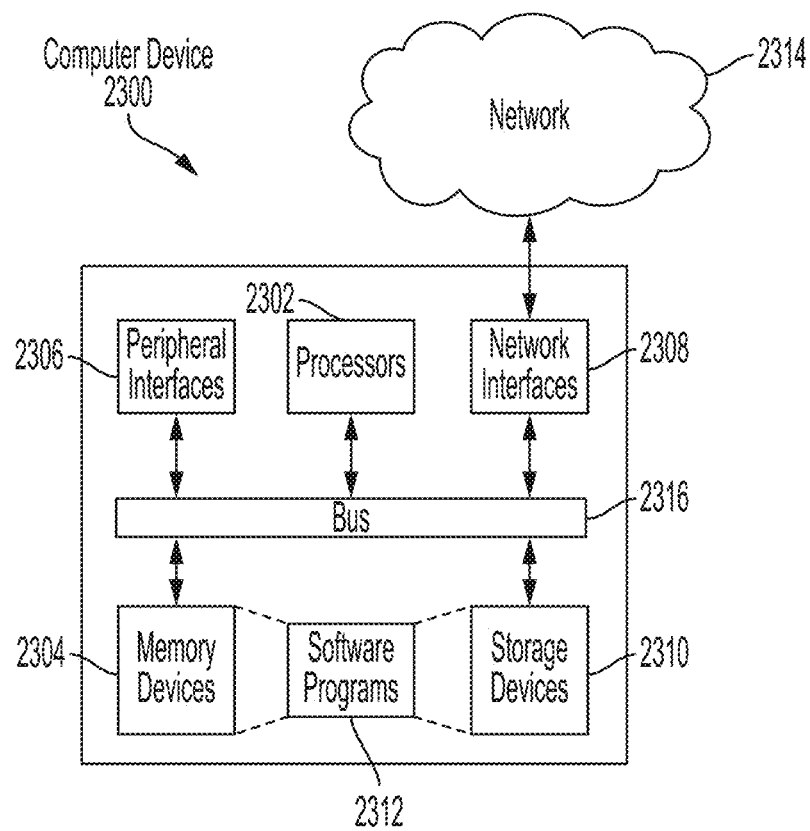
FIG. 23 is an example of a hardware configuration for a computer device, according to examples of the present disclosure.

FIG. 23 is an example of a hardware configuration for a computer device 2300, which can be used to perform one or more of the processes described above and/or to implement CT system 102 and/or control system 118 described above. The computer device 2300 can be any type of computer devices, such as desktops, laptops, servers, etc., or mobile devices, such as smart telephones, tablet computers, cellular telephones, personal digital assistants, etc. As illustrated in FIG. 23, the computer device 2300 can include one or more processors 2302 of varying core configurations and clock frequencies. The computer device 2300 can also include one or more memory devices 2304 that serve as a main memory during the operation of the computer device 2300. For example, during operation, a copy of the software that supports the above-described operations can be stored in the one or more memory devices 2304. The computer device 2300 can also include one or more peripheral interfaces 2306, such as keyboards, mice, touchpads, computer screens, touchscreens, etc., for enabling human interaction with and manipulation of the computer device 2300.

The computer device 2300 can also include one or more network interfaces 2308 for communicating via one or more networks, such as Ethernet adapters, wireless transceivers, or serial network components, for communicating over wired or wireless media using protocols. The computer device 2300 can also include one or more storage devices 2310 of varying physical dimensions and storage capacities, such as flash drives, hard drives, random access memory, etc., for storing data, such as images, files, and program instructions for execution by the one or more processors 2302.

Additionally, the computer device 2300 can include one or more software programs 2312 that enable the functionality described above. The one or more software programs 2312 can include instructions that cause the one or more processors 2302 to perform the processes, functions, and operations described herein, for example, with respect to the processes of FIGS. 2, 12, 14, 21, and/or 22. Copies of the one or more software programs 2312 can be stored in the one or more memory devices 2304 and/or on in the one or more storage devices 2310. Likewise, the data utilized by one or more software programs 2312 can be stored in the one or more memory devices 2304 and/or on in the one or more storage devices 2310. Data bus 2316 provides a data communication pathway between the various components of the computer device 2300.

In implementations, the computer device 2300 can communicate with other devices via a network 2314. The other devices can be any types of devices as described above. The network 2314 can be any type of network, such as a local area network, a wide-area network, a virtual private network, the Internet, an intranet, an extranet, a public switched telephone network, an infrared network, a wireless network, and any combination thereof. The network 2314 can support communications using any of a variety of commercially-available protocols, such as TCP/IP, UDP, OSI, FTP, UPnP, NFS, CIFS, AppleTalk, and the like. The network 2314 can be, for example, a local area network, a wide-area network, a virtual private network, the Internet, an intranet, an extranet, a public switched telephone network, an infrared network, a wireless network, and any combination thereof.

The computer device 2300 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers, or other network devices may be stored locally and/or remotely, as appropriate.

In implementations, the components of the computer device 2300 as described above need not be enclosed within a single enclosure or even located in close proximity to one another. Those skilled in the art will appreciate that the above-described componentry are examples only, as the computer device 2300 can include any type of hardware componentry, including any necessary accompanying firmware or software, for performing the disclosed implementations. The computer device 2300 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The foregoing description is illustrative, and variations in configuration and implementation can occur to persons skilled in the art. For instance, the various illustrative logics, logical blocks, modules, and circuits described in connection with the embodiments disclosed herein can be implemented or performed with a general purpose processor, a digital signal processor (DSP), an application specific integrated circuit (ASIC), a field programmable gate array (FPGA), cryptographic co-processor, or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Compared to existing MAR solutions, the MAA method has several advantages. First, as few as two scout views are acquired besides the nominal 3D scan. There is no extra radiation for patients since scout views are typically acquired as a standard practice to confirm positioning of the patient. Second, no prior information on the shape of the metal inserts or a pre-instrumentation 3D scan of the patient is required. Third, the underlying algorithm for optimal trajectory (tilt angle) calculation is independent of the existing reconstruction and artifacts correction pipeline and can be deployed as a separate module, making it much easier to be integrated into current CBCT systems. Finally, as a hardware-based solution, it is more robust and does not bare the risk of introducing unrealistic information (through interpolation etc.) into the reconstructed volume, compared to its software-based counterparts.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents. Information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

Further, the disclosure comprises embodiments according to the following clauses:

Clause 1. A method for metal artifact avoidance in 3D x-ray imaging, the method comprising:
determining a 3D location of metal in an object or volume of interest to be scanned;
estimating a source-detector orbit that will reduce the severity of metal artifacts;
moving an imaging system to locations consistent with the source-detector orbit that was estimated or to locations close to the source-detector orbit that was estimated and within existing spatial constraints; and
scanning the object according to the source-detector orbit.

Clause 2. The method of clause 1, wherein the determining further comprises one or more of the following: performing an initial 3D scan of the object or volume of interest, acquiring one or more x-ray projection images of the object or volume of interest, or using a tracking system comprising one or more cameras or electromagnetic trackers to locate the metal.

Clause 3. The method of clauses 1 or 2, wherein the source-detector orbit comprises a position and orientation of an x-ray source and a detector for projections to be acquired in the in 3D x-ray imaging.

Clause 4. The method of clauses 1-3, wherein the estimating the source-detector orbit further comprises computing an objective function that is based on the 3D location of the metal that was determined, wherein the objective function describes a characteristic that is associated with metal artifacts in 3D image reconstruction.

Clause 5. The method of clauses 1-4, wherein the characteristic comprises an estimation of a spectral shift, an attenuation, or combinations thereof.

Clause 6. The method of clauses 1-5, wherein the objective function is based on one or more of: a range of a metric map along a rotation axis of a gantry, a standard deviation of a metric map along a rotation axis of a gantry, a maximum of the metric map along the rotation axis of the gantry, a sum of metric maps for a range of rotation angles of the gantry.

Clause 7. The method of clauses 1-6, wherein the severity of metal artifacts is reduced compared to a circular path in a plane perpendicular to a long axis of the object.

Clause 8. The method of clauses 1-7, wherein the scanning further comprises acquiring a plurality of x-ray projections along the source-detector orbit and forming a 3D image reconstruction of the object.

Clause 9. The method of clauses 1-8, wherein the forming the 3D image reconstruction further comprises performing one or more 3D image reconstruction algorithms comprising 3D filtered backprojection, model-based image reconstruction, deep-learning, or neural network reconstruction.

Further, the disclosure comprises embodiments according to the following clauses:

Clause 1. A 3-D x-ray imaging system comprising:
a 3-D x-ray imaging device comprising a gantry that is movable in a plurality of tilt angles along a tilt axis and a plurality of rotation angles along a rotation axis; and
a hardware-processor configured to execute instructions comprising:
determining a 3D location of metal in an object or volume of interest to be scanned;
estimating a source-detector orbit that will reduce the severity of metal artifacts;
moving an imaging system to locations consistent with the source-detector orbit that was estimated or to locations close to the source-detector orbit that was estimated and within existing spatial constraints; and
scanning the object according to the source-detector orbit.

Clause 2. The 3-D x-ray imaging system of clause 1, wherein the determining further comprises one or more of the following: performing an initial 3D scan of the object or volume of interest, acquiring one or more x-ray projection images of the object or volume of interest, or using a tracking system comprising one or more cameras or electromagnetic trackers to locate the metal.

Clause 3. The 3-D x-ray imaging system of clauses 1 or 2, wherein the source-detector orbit comprises a position and orientation of an x-ray source and a detector for projections to be acquired in the in 3D x-ray imaging.

Clause 4. The 3-D x-ray imaging system of clauses 1-3, wherein the estimating the source-detector orbit further comprises computing an objective function that is based on the 3D location of the metal that was determined, wherein the objective function describes a characteristic that is associated with metal artifacts in 3D image reconstruction.

Clause 5. The 3-D x-ray imaging system of clauses 1-4, wherein the characteristic comprises an estimation of a spectral shift, an attenuation, or combinations thereof.

Clause 6. The 3-D x-ray imaging system of clauses 1-5, wherein the objective function is based on one or more of: a range in a metric map along a rotation axis of a gantry, a standard deviation of a metric map along a rotation axis of a gantry, a maximum of the metric map along the rotation axis of the gantry, a sum of metric maps for a range of rotation angles of the gantry.

Clause 7. The 3-D x-ray imaging system of clauses 1-6, wherein the severity of metal artifacts is reduced compared to a circular path in a plane perpendicular to a long axis of the object.

Clause 8. The 3-D x-ray imaging system of clauses 1-7, wherein the scanning further comprises acquiring a plurality of x-ray projections along the source-detector orbit and forming a 3D image reconstruction of the object.

Clause 9. The 3-D x-ray imaging system of clauses 1-8, wherein the forming the 3D image reconstruction further comprises performing one or more 3D image reconstruction algorithms comprising 3D filtered backprojection, model-based image reconstruction, deep-learning, or neural network reconstruction.

Notwithstanding that the numerical ranges and parameters setting forth the broad scope of the present teachings are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less than 10" can assume negative values, e.g. $-1, -2, -3, -10, -20, -30$, etc.

While the present teachings have been illustrated with respect to one or more implementations, alterations and/or modifications can be made to the illustrated examples without departing from the spirit and scope of the appended claims. For example, it will be appreciated that while the process is described as a series of acts or events, the present teachings are not limited by the ordering of such acts or events. Some acts may occur in different orders and/or concurrently with other acts or events apart from those described herein. Also, not all process stages may be required to implement a methodology in accordance with one or more aspects or implementations of the present teachings. It will be appreciated that structural components and/or processing stages can be added or existing structural components and/or processing stages can be removed or modified. Further, one or more of the acts depicted herein may be carried out in one or more separate acts and/or phases. Furthermore, to the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. As used herein, the term "one or more of" with respect to a listing of items such as, for example, A and B, means A alone, B alone, or A and B. Further, in the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about" indicates that the value listed may be somewhat altered, as long as the alteration does not result in nonconformance of the process or structure to the illustrated implementation. Finally, "exemplary" indicates the description is used as an example, rather than implying that it is an ideal. Other implementations of the present teachings will be apparent to those skilled in the art from consideration of the specification and practice of the disclosure herein. It is intended that the specification and examples be considered as exemplary only, with a true scope and spirit of the present teachings being indicated by the following claims.

What is claimed is:

1. A method for metal artifact avoidance in 3D x-ray imaging, the method comprising:
   determining a 3D location of metal in an object or volume of interest to be scanned;
   estimating a source-detector orbit that will reduce severity of metal artifacts, wherein the source-detector orbit is a non-circular orbit that is defined by a tilt angle and a rotation angle of a gantry arm are varied during a scanning operation, wherein the estimating the source-detector orbit further comprises computing an objective function that is based on the 3D location of the metal that was determined, wherein the objective function describes a spectral shift that is associated with metal artifacts in 3D image reconstruction;
   moving an imaging system to locations consistent with the source-detector orbit that was estimated or to locations close to the source-detector orbit that was estimated and within existing spatial constraints; and
   scanning the object or the volume of interest according to the source-detector orbit.

2. The method of claim 1, wherein the determining further comprises one or more of the following: performing an initial 3D scan of the object or volume of interest, acquiring one or more x-ray projection images of the object or volume of interest, or using a tracking system comprising one or more cameras or electromagnetic trackers to locate the metal.

3. The method of claim 1, wherein the source-detector orbit comprises a position and orientation of an x-ray source and a detector for projections to be acquired in the 3D x-ray imaging.

4. The method of claim 1, wherein the objective function is further based on one or more of: a range in a metric map along a rotation axis of a gantry, a standard deviation of a metric map along a rotation axis of a gantry, a maximum of the metric map along the rotation axis of the gantry, a sum of metric maps for a range of rotation angles of the gantry.

5. The method of claim 1, wherein the severity of metal artifacts is reduced compared to a circular path in a plane perpendicular to a long axis of the object.

6. The method of claim 1, wherein the scanning further comprises acquiring a plurality of x-ray projections along the source-detector orbit and forming a 3D image reconstruction of the object.

7. The method of claim 6, wherein the forming the 3D image reconstruction further comprises performing one or more 3D image reconstruction algorithms comprising 3D filtered backprojection, other analytical methods for 3D image reconstruction, model-based image reconstruction, deep-learning, or neural network reconstruction.

8. A 3-D x-ray imaging system comprising:
a 3-D x-ray imaging device comprising a gantry that is movable in a plurality of tilt angles along a tilt axis and a plurality of rotation angles along a rotation axis; and
a hardware-processor configured to execute instructions comprising:
determining a 3D location of metal in an object or volume of interest to be scanned;
estimating a source-detector orbit that will reduce severity of metal artifacts, wherein the source-detector orbit is a non-circular orbit that is defined by a tilt angle and a rotation angle of a gantry arm are varied during a scanning operation, wherein the estimating the source-detector orbit further comprises computing an objective function that is based on the 3D location of the metal that was determined, wherein the objective function describes a spectral shift that is associated with metal artifacts in 3D image reconstruction;
moving an imaging system to locations consistent with the source-detector orbit that was estimated or to locations close to the source-detector orbit that was estimated and within existing spatial constraints; and
scanning the object or the volume of interest according to the source-detector orbit.

9. The 3-D x-ray imaging system of claim 8, wherein the determining further comprises one or more of the following: performing an initial 3D scan of the object or volume of interest, acquiring one or more x-ray projection images of the object or volume of interest, or using a tracking system comprising one or more cameras or electromagnetic trackers to locate the metal.

10. The 3-D x-ray imaging system of claim 8, wherein the source-detector orbit comprises a position and orientation of an x-ray source and a detector for projections to be acquired in 3D x-ray imaging.

11. The 3-D x-ray imaging system of claim 8, wherein the objective function is further based on one or more of: a range of a metric map along a rotation axis of a gantry, a standard deviation of a metric map along a rotation axis of a gantry, a maximum of the metric map along the rotation axis of the gantry, a sum of metric maps for a range of rotation angles of the gantry.

12. The 3-D x-ray imaging system of claim 8, wherein the severity of metal artifacts is reduced compared to a circular path in a plane perpendicular to a long axis of the object.

13. The 3-D x-ray imaging system of claim 8, wherein the scanning further comprises acquiring a plurality of x-ray projections along the source-detector orbit and forming a 3D image reconstruction of the object.

14. The 3-D x-ray imaging system of claim 13, wherein the forming the 3D image reconstruction further comprises performing one or more 3D image reconstruction algorithms comprising 3D filtered backprojection, other analytical methods for 3D image reconstruction, model-based image reconstruction, deep-learning, or neural network reconstruction.

15. A non-transitory computer readable medium comprising instructions that when executed by a hardware processor are configured to perform a method for metal artifact avoidance in 3D x-ray imaging, the method comprising:
determining a 3D location of metal in an object or volume of interest to be scanned;
estimating a source-detector orbit that will reduce severity of metal artifacts, wherein the source-detector orbit is a non-circular orbit that is defined by a tilt angle and a rotation angle of a gantry arm are varied during a scanning operation, wherein the estimating the source-detector orbit further comprises computing an objective function that is based on the 3D location of the metal that was determined, wherein the objective function describes a spectral shift that is associated with metal artifacts in 3D image reconstruction;
moving an imaging system to locations consistent with the source-detector orbit that was estimated or to locations close to the source-detector orbit that was estimated and within existing spatial constraints; and
scanning the object or the volume of interest according to the source-detector orbit.

16. The non-transitory computer readable medium of claim 15, wherein the determining further comprises one or more of the following: performing an initial 3D scan of the object or volume of interest, acquiring one or more x-ray projection images of the object or volume of interest, or using a tracking system comprising one or more cameras or electromagnetic trackers to locate the metal.

17. The non-transitory computer readable medium of claim 15, wherein the source-detector orbit comprises a position and orientation of an x-ray source and a detector for projections to be acquired in the 3D x-ray imaging.

18. The non-transitory computer readable medium of claim 15, wherein the objective function is further based on one or more of: a range in a metric map along a rotation axis of a gantry, a standard deviation of a metric map along a rotation axis of a gantry, a maximum of the metric map along the rotation axis of the gantry, a sum of metric maps for a range of rotation angles of the gantry.

19. The non-transitory computer readable medium of claim 15, wherein the severity of metal artifacts is reduced compared to a circular path in a plane perpendicular to a long axis of the object.

20. The non-transitory computer readable medium of claim 15, wherein the scanning further comprises acquiring a plurality of x-ray projections along the source-detector orbit and forming a 3D image reconstruction of the object.

* * * * *